United States Patent
Matsui et al.

(10) Patent No.: US 9,163,081 B2
(45) Date of Patent: Oct. 20, 2015

(54) ANTIBODY RECOGNIZING C-DOMAIN OF MIDKINE

(75) Inventors: Takashi Matsui, Kanagawa (JP); Takashi Muramatsu, Aichi (JP); Masatoshi Hayashibara, Tokyo (JP); Takanori Ito, Kanagawa (JP); Tsukasa Uno, Yokohama (JP); Sadatoshi Sakuma, Kanagawa (JP)

(73) Assignee: Medical Therapies Limited (AU)

( * ) Notice: Subject to any disclaimer, the term of this patent is extended or adjusted under 35 U.S.C. 154(b) by 1270 days.

(21) Appl. No.: 12/312,522

(22) PCT Filed: Nov. 13, 2007

(86) PCT No.: PCT/JP2007/001238
§ 371 (c)(1),
(2), (4) Date: May 14, 2009

(87) PCT Pub. No.: WO2008/059616
PCT Pub. Date: May 22, 2008

(65) Prior Publication Data
US 2010/0311187 A1    Dec. 9, 2010

(30) Foreign Application Priority Data
Nov. 14, 2006  (JP) .................. 2006-308466

(51) Int. Cl.
*C07K 16/22*    (2006.01)
*G01N 33/68*    (2006.01)
*A61K 39/395*   (2006.01)
*A61K 39/00*    (2006.01)

(52) U.S. Cl.
CPC ............ *C07K 16/22* (2013.01); *A61K 39/3955* (2013.01); *G01N 33/6854* (2013.01); *G01N 33/6857* (2013.01); *A61K 2039/505* (2013.01); *C07K 2316/96* (2013.01); *C07K 2317/565* (2013.01)

(58) Field of Classification Search
CPC .................... A61K 39/3955; A61K 2039/505; C07K 16/22; C07K 2316/96; C07K 2317/565; C07K 2317/76; G01N 33/6854; G01N 33/6857
USPC ......... 435/7.1, 7.21, 7.23, 40.52, 69.1, 70.21, 435/451, 452, 328, 331, 335; 436/518, 536; 530/387.3, 387.9, 388.23, 388.24, 530/388.8, 388.85, 389.1, 389.2, 389.7, 530/391.1; 424/139.1, 145.1, 155.1, 156.1
See application file for complete search history.

(56) References Cited

U.S. PATENT DOCUMENTS

| | | | |
|---|---|---|---|
| 6,083,907 A | 7/2000 | Uchida et al. | |
| 2004/0219614 A1 | 11/2004 | Mitsumoto et al. | |
| 2007/0154949 A1 | 7/2007 | Mitsumoto et al. | |
| 2010/0092488 A1 | 4/2010 | Suzumura et al. | |
| 2011/0086906 A1 | 4/2011 | Suzumura et al. | |

FOREIGN PATENT DOCUMENTS

| | | |
|---|---|---|
| CA | 2220854 A1 | 7/1999 |
| EP | 1964574 A1 | 9/2008 |
| JP | 09-095454 A | 4/1997 |
| JP | 2002-085058 A | 3/2002 |
| JP | 2002-125666 A | 5/2002 |
| WO | WO-2007/055378 A1 | 5/2007 |

OTHER PUBLICATIONS

Hellström et al., 1985. In Monoclonal Antibodies for Cancer Detection and Therapy (Baldwin et al, eds.), Academic Press, London. p. 20.*
"European Application Serial No. 07828015.3, European Search Report mailed Apr. 18, 2011", 9 pgs.
"International Application Serial No. PCT/JP2007/001238, International Search Report mailed Dec. 18, 2007", (w/ English Translation), 4 pgs.
"International Application Serial No. PCT/JP2007/001238, Written Opinion mailed Dec. 18, 2007", (w/ English Translation), 9 pgs.
Dansithong, W., et al., "Production and characterization of a bacterial single-chain Fv fragment specific to human truncated midkine", *Cancer Letters*, 164, (2001), 169-176.
Inoh, K., et al., "Doxorubicin-Conjugated Anti-Midkine Monoclonal Antibody as a Potential Anti-Tumor Drug", *Japanese Journal of Clinical Oncology*, 36(4), (2006), 5 pgs.
Iwasaki, W., et al., "Solution structure of midkine, a new heparin-binding growth factor", *The EmBo Journal*. 16(23). (1997), 6936-6946.
Kato, S., et al., "Monoclonal Antibody to Human Midkine Reveals Increased Midkine Expression in Human Brain Tumors", *Journal of Neuropathology and Experimental Neurology*, 58(5), (1999), 430-441.
Kojima, S., et al., "Synthetic Peptides Derived from Midkine Enhance Plasminogen Activator Activity in Bovine Aortic Endothelial Cells", *Biochem. Biophys. Res. Commun.*, 206(2), (1995), 468-473.

(Continued)

*Primary Examiner* — Gail R Gabel
*Assistant Examiner* — James L Grun
(74) *Attorney, Agent, or Firm* — Schwegman Lundberg & Woessner, P.A.

(57) ABSTRACT

It is intended to provide an antibody which inhibits the function of midkine. An antibody which recognizes an epitope consisting of amino acid residues 62 to 104 of midkine or a fragment thereof; DNA encoding the antibody or a fragment thereof; a recombinant vector which contains the DNA; a transformant which has the vector or a hybridoma which produces the antibody; a method for producing the antibody by allowing the transformant or hybridoma to produce the antibody or a fragment thereof and collecting the resulting antibody or fragment thereof; a pharmaceutical composition containing the antibody or a fragment thereof as an active ingredient; and a diagnostic agent containing the antibody or a fragment thereof as an active ingredient.

12 Claims, 2 Drawing Sheets

(56) References Cited

OTHER PUBLICATIONS

Maehara, H., et al., "Midkine as a novel target for antibody theraphy in osteosarcoma", *Biochemical and Biophysical Research Communications*, 358(3), (Abstract Only), (2007), 757-762.

Muramatsu, H., et al., "Midkine, A Retinoic Acid-Inducible Growth/Differentiation Factor: Immunochemical Evidence for the Function and Distribution", *Developmental Biology*, 159(2), (1993), 392-402.

Muramatsu, T., et al., "Midkine and Pieiotrophin: Two Related Proteins Involved in Development, Survival, Inflammation and Tumorigenesis", *Journal of Biochemistry*, 132(3), (2002), 359-371.

Zhang, Q-Y., et al., "Expression of midkine fusion protein and preparation and application of its monoclonal antibodies". *Database Medline*—Accession No. NLM16143068, (English Abstract Only), (Sep. 2005), 2 pgs.

\* cited by examiner

ANTIBODY RECOGNIZING C-DOMAIN OF MIDKINE

RELATED APPLICATIONS

This application is a nationalization under 35 U.S.C. 371 of PCT/JP2007/001238, filed Nov. 13, 2007 and published as WO 2008/059616 A1, on May 22, 2008, which claimed priority under 35 U.S.C. 119 to Japanese Application No. 2006308466, field Nov. 14, 2006; which applications and publication are incorporated herein by reference and made a part hereof.

TECHNICAL FIELD

The present invention relates to an antibody against midkine.

BACKGROUND ART

Midkine (hereinafter, referred to as "MK") is a growth/differentiation factor found as a product of a gene transiently expressed in the stage of retinoic acid-induced differentiation of embryonal carcinoma (EC) cells and is a polypeptide of 13 kDa in molecular weight rich in basic amino acids and cysteine (see e.g., Non-Patent Documents 1 and 2).

MK is known to have various biological activities. It is known that MK expression is increased in human cancer cells. This increase in expression has been confirmed in various cancers such as esophageal cancer, thyroid cancer, urinary bladder cancer, colon cancer, stomach cancer, pancreatic cancer, thoracic cancer, liver cancer, lung cancer, breast cancer, neuroblastoma, glioblastoma, uterine cancer, ovarian cancer, and Wilms tumor (see e.g., Patent Document 1 and Non-Patent Document 3). Moreover, MK is thought to promote the survival and migration of cancer cells, promote angiogenesis, and contribute to cancer progression.

Moreover, MK is known as a molecule that plays a central role in the stage of inflammation formation. For example, it is known that neointimal formation after vascular injury and nephritis onset during ischemic injury are suppressed in knockout mice deficient in MK genes. Moreover, it is also known that rheumatism models and postoperative adhesion are significantly suppressed in such knockout mice (see e.g., Patent Documents 2, 3, and 4). Thus, MK is known to participate in inflammatory diseases such as arthritis, autoimmune disease, rheumatic arthritis (rheumatoid arthritis (RA) or osteoarthritis (OA)), multiple sclerosis, postoperative adhesion, inflammatory bowel disease, psoriasis, lupus, asthma, and neutrophil dysfunction. Furthermore, MK is known to promote the movement (migration) of inflammatory cells such as macrophages or neutrophils. Since this movement is necessary for the establishment of inflammation, it is thought that deficiency of MK probably prevents diseases based on inflammation (see e.g., Patent Document 5).

Moreover, since MK exists at an increased level in peritoneal fluids of women with progressive endometriosis and stimulates the growth of cultured endometrial stromal cells, MK is known to participate in the onset and progression of endometriosis (see e.g., Patent Document 6).

Furthermore, since MK has vascular intimal thickening effects, MK is known to participate in occlusive vascular diseases such as post-revascularization restenosis, coronary occlusive disease, cerebrovascular occlusive disease, renovascular occlusive disease, peripheral occlusive disease, arteriosclerosis, and cerebral infarction (see e.g., Patent Document 2).

Cell migration is known to be important for mechanisms underlying cancer cell infiltration/metastasis, intimal thickening in atherosclerotic lesions, angiogenesis, and so on. Moreover, inflammatory cell migration is known to deeply participate in cardiovascular diseases such as angina pectoris, myocardial infarction, cerebral infarction, cerebral hemorrhage, and hypertension.

Moreover, the three-dimensional structure of MK has been determined by NMR and reported (see e.g., Non-Patent Document 4). MK is composed of: an N-terminal fragment (hereinafter, referred to as an "N-fragment") consisting of amino acid residues 1 to 52; a C-terminal fragment (hereinafter, referred to as a "C-fragment") consisting of amino acid residues 62 to 121; and a loop region (amino acid residues 53 to 61) (hereinafter, referred to as a "loop") that links these fragments.

Each of the N- and C-fragments is mainly composed of: a portion having a three-dimensional structure consisting of three antiparallel β-sheets (hereinafter, referred to as a "domain"; the domain (consisting of amino acid residues 15 to 52) in the N-fragment is referred to as an "N-domain", and the domain (consisting of amino acid residues 62 to 104) in the C-fragment is referred to as a "C-domain"); and a terminally located portion devoid of the domain that does not assume a particular three-dimensional structure (hereinafter, referred to as a "tail"; the tail (consisting of amino acid residues 1 to 14) in the N-fragment is referred to as an "N-tail", and the tail (consisting of amino acid residues 105 to 121) in the C-fragment is referred to as a "C-tail"). Basic amino acids on the C-domain surface form two clusters: a cluster consisting of lysine 79, arginine 81, and lysine 102 (cluster I) and a cluster consisting of lysine 86, lysine 87, and arginine 89 (cluster II) (see e.g., Non-Patent Document 4). Both the clusters are known to participate in heparin-binding ability (see e.g., Non-Patent Documents 4 and 5).

On the other hand, regarding antibodies against MK, mice immunized with human MK proteins as immunogens are considered to hardly recognize the MK proteins as foreign heterologous proteins in vivo, due to high conservation of MK proteins among species and 87% homology between human and mouse MK amino acid sequences. Thus, it is known that anti-human MK monoclonal antibodies are obtained using MK gene-knockout mice (see e.g., Patent Document 7). However, there have been no previous reports on epitopes on MK recognized by anti-human MK antibodies having the activity of inhibiting MK functions.

Patent Document 1: Japanese Patent Laid-Open No. 6-172218
Patent Document 2: Pamphlet of WO2000/10608
Patent Document 3: Pamphlet of WO2004/078210
Patent Document 4: Pamphlet of WO2004/085642
Patent Document 5: Pamphlet of WO1999/03493
Patent Document 6: Pamphlet of WO2006/016571
Patent Document 7: Japanese Patent Laid-Open No. 2002-85058
Non-Patent Document 1: Kadomatsu, K. et al.: (1988) Biochem. Biophys. Res. Commun., 151: p. 1312-1318
Non-Patent Document 2: Tomokura, M. et al.: (1999) J. Biol. Chem, 265: p. 10765-10770
Non-Patent Document 3: Muramatsu, T.: (2002) J. Biochem. 132, p. 359-371
Non-Patent Document 4: Iwasaki, W. et al.: (1997) EMBO J. 16, p. 6936-6946

Non-Patent Document 5: Asai, S. et al.: (1995) Biochem. Biophys. Res Commun. 206, P. 468-473.

DISCLOSURE OF THE INVENTION

Problems to be Solved by the Invention

An object of the present invention is to provide an antibody or a fragment thereof which recognizes an epitope on MK.

Means for Solving the Problems

The present inventors prepared antibodies against human MK and found antibodies having the activity of inhibiting the cell migration functions of MK from among the obtained antibodies. The present inventors conducted an EAE model animal test using the obtained antibodies and consequently found that these antibodies have excellent inhibitory effects on EAE onset. Moreover, the present inventors found epitopes on MK recognized by these antibodies having the activity of inhibiting MK functions. Furthermore, the present inventors conducted diligent studies on common characteristics among the epitopes on MK recognized by these antibodies and consequently found that all the antibodies bind to sites with a high electrostatic potential in the three-dimensional structure of MK and that these sites contribute to the expression of MK functions. Based on these findings, the present invention has been completed.

Specifically, the present invention relates to an antibody or a fragment thereof which recognizes an epitope located at amino acid residues 62 to 104 of MK, an antibody or a fragment thereof which recognizes at least a portion of a high electrostatic potential cluster located at amino acid residues 62 to 104 of MK, a DNA encoding the antibody or the fragment thereof, a recombinant vector comprising the DNA, a transformant having the vector, a method for producing the antibody or the fragment thereof, comprising allowing the transformant to produce the antibody or the fragment thereof and collecting the antibody or the fragment thereof, a pharmaceutical composition comprising the antibody or the fragment thereof as an active ingredient, and a diagnostic agent comprising the antibody or the fragment thereof. Moreover, the present invention relates to a method for screening a substance that recognizes a epitope on MK recognized by the antibody or the fragment thereof which recognizes an epitope located at amino acid residues 62 to 104 of MK.

More preferably, the present invention relates to the following (1) to (41):

(1) an antibody or a fragment thereof which recognizes at least a portion of an epitope located at amino acid residues 62 to 104 of MK;

(2) an antibody or a fragment thereof which recognizes at least a portion of an epitope located at amino acid residues 64 to 73 and amino acid residues 78 to 101 of MK;

(3) an antibody or a fragment thereof which recognizes at least a portion of an epitope located at amino acid residues 64 to 73, amino acid residues 64 to 69, amino acid residues 64 to 67, and amino acid residues 84 to 96 of MK;

(4) an antibody or a fragment thereof which recognizes at least a portion of an epitope located at amino acid residues 64 to 66 and amino acid residues 87 to 96 of MK;

(5) an antibody or a fragment thereof which recognizes at least a portion of an epitope located at amino acids selected from tyrosine 64, lysine 65, phenylalanine 66, glutamic acid 67, tryptophan 69, aspartic acid 73, threonine 84, lysine 86, and glutamic acid 96 of MK;

(6) an antibody or a fragment thereof which recognizes at least a portion of an epitope located at amino acids selected from tyrosine 64, phenylalanine 66, lysine 87, tyrosine 90, and glutamic acid 96 of MK;

(7) the antibody according to any one of (1) to (6) or a fragment thereof, wherein the epitope is a conformational epitope;

(8) the antibody according to (7) or a fragment thereof, wherein the conformational epitope is an antiparallel β-sheet epitope;

(9) the antibody according to any one of (1) to (8) or a fragment thereof which recognizes at least three amino acids of the epitope;

(10) an antibody or a fragment thereof which recognizes at least a portion of a high electrostatic potential cluster located at amino acid residues 62 to 104 of MK;

(11) the antibody according to (10) or a fragment thereof which recognizes at least three amino acids of the cluster;

(12) an antibody or a fragment thereof which recognizes at least one amino acid selected from amino acid residues 62 to 64, amino acid residue 66, amino acid residues 68 to 70, amino acid residue 72, amino acid residue 79, amino acid residue 81, amino acid residues 85 to 89, amino acid residue 102, and amino acid residue 103 of MK;

(13) an antibody or a fragment thereof which recognizes at least one amino acid selected from lysine 63, lysine 79, arginine 81, lysine 86, lysine 87, arginine 89, and lysine 102 of MK;

(14) an anti-MK antibody or a fragment thereof, wherein heavy chain CDR3 has the amino acid sequence represented by SEQ ID NO: 15 or 21 or a conservatively modified amino acid sequence thereof;

(15) the monoclonal antibody wherein heavy chain CDR1 has the amino acid sequence represented by SEQ ID NO: 13 or 19 or a conservatively modified amino acid sequence thereof, heavy chain variable domain CDR2 has the amino acid sequence represented by SEQ ID NO: 14 or 20 or a conservatively modified amino acid sequence thereof, light chain variable region CDR1 has the amino acid sequence represented by SEQ ID NO: 16 or 22 or a conservatively modified amino acid sequence thereof, light chain variable region CDR2 has the amino acid sequence represented by SEQ ID NO: 17 or 23 or a conservatively modified amino acid sequence thereof, and light chain CDR3 has the amino acid sequence represented by SEQ ID NO: 18 or 24 or a conservatively modified amino acid sequence thereof;

(16) an anti-MK monoclonal antibody or a fragment thereof, wherein heavy chain CDR3 has the amino acid sequence represented by SEQ ID NO: 15 or 21 or an amino acid sequence exhibiting 95% or higher homology thereto;

(17) the monoclonal antibody or a fragment thereof, wherein heavy chain CDR1 has the amino acid sequence represented by SEQ ID NO: 13 or 19 or an amino acid sequence exhibiting 95% or higher homology thereto, heavy chain CDR2 has the amino acid sequence represented by SEQ ID NO: 14 or 20 or an amino acid sequence exhibiting 95% or higher homology thereto, light chain CDR1 has the amino acid sequence represented by SEQ ID NO: 16 or 22 or an amino acid sequence exhibiting 95% or higher homology thereto, light chain variable region CDR2 has the amino acid sequence represented by SEQ ID NO: 17 or 23 or an amino acid sequence exhibiting 95% or higher homology thereto, and light chain CDR3 has the amino acid sequence represented by SEQ ID NO: 18 or 24 or an amino acid sequence exhibiting 95% or higher homology thereto;

(18) an anti-MK monoclonal antibody or a fragment thereof, wherein heavy chain CDR1 has the amino acid sequence represented by SEQ ID NO: 13, heavy chain CDR2 has the amino acid sequence represented by SEQ ID NO: 14, a conservatively modified amino acid sequence thereof, or an amino acid sequence exhibiting 95% or higher homology thereto, heavy chain CDR3 has the amino acid sequence represented by SEQ ID NO: 15, a conservatively modified amino acid sequence thereof, or an amino acid sequence exhibiting 95% or higher homology thereto, light chain CDR1 has the amino acid sequence represented by SEQ ID NO: 16, a conservatively modified amino acid sequence thereof, or an amino acid sequence exhibiting 95% or higher homology thereto, light chain CDR2 has the amino acid sequence represented by SEQ ID NO: 17, a conservatively modified amino acid sequence thereof, or an amino acid sequence exhibiting 95% or higher homology thereto, and light chain CDR3 has the amino acid sequence represented by SEQ ID NO: 18, a conservatively modified amino acid sequence thereof, or an amino acid sequence exhibiting 95% or higher homology thereto;

(19) an anti-MK monoclonal antibody or a fragment thereof, wherein heavy chain CDR1 has the amino acid sequence represented by SEQ ID NO: 19, heavy chain CDR2 has the amino acid sequence represented by SEQ ID NO: 20, a conservatively modified amino acid sequence thereof, or an amino acid sequence exhibiting 95% or higher homology thereto, heavy chain CDR3 has the amino acid sequence represented by SEQ ID NO: 21, a conservatively modified amino acid sequence thereof, or an amino acid sequence exhibiting 95% or higher homology thereto, light chain CDR1 has the amino acid sequence represented by SEQ ID NO: 22, a conservatively modified amino acid sequence thereof, or an amino acid sequence exhibiting 95% or higher homology thereto, light chain CDR2 has the amino acid sequence represented by SEQ ID NO: 23, a conservatively modified amino acid sequence thereof, or an amino acid sequence exhibiting 95% or higher homology thereto, and light chain CDR3 has the amino acid sequence represented by SEQ ID NO: 24, a conservatively modified amino acid sequence thereof, or an amino acid sequence exhibiting 95% or higher homology thereto;

(20) an anti-MK monoclonal antibody or a fragment thereof, wherein heavy chain CDR1 has the amino acid sequence represented by SEQ ID NO: 13, heavy chain CDR2 has the amino acid sequence represented by SEQ ID NO: 14, heavy chain CDR3 has the amino acid sequence represented by SEQ ID NO: 15, light chain CDR1 has the amino acid sequence represented by SEQ ID NO: 16, light chain CDR2 has the amino acid sequence represented by SEQ ID NO: 17, and light chain CDR3 has the amino acid sequence represented by SEQ ID NO: 18;

(21) an anti-MK monoclonal antibody or a fragment thereof, wherein heavy chain CDR1 has the amino acid sequence represented by SEQ ID NO: 19, heavy chain CDR2 has the amino acid sequence represented by SEQ ID NO: 20, heavy chain CDR3 has the amino acid sequence represented by SEQ ID NO: 21, light chain CDR1 has the amino acid sequence represented by SEQ ID NO: 22, light chain CDR2 has the amino acid sequence represented by SEQ ID NO: 23, and light chain CDR3 has the amino acid sequence represented by SEQ ID NO: 24;

(22) an antibody or a fragment thereof which recognizes an epitope on MK recognized by a monoclonal antibody according to any one of (14) to (21);

(23) the antibody according to any one of (1) to (22) or a fragment thereof which specifically binds to MK;

(24) the antibody according to any one of (1) to (23) or a fragment thereof, wherein the MK is human MK;

(25) the antibody according to any one of (1) to (24), wherein the antibody is a monoclonal antibody;

(26) the antibody according to any one of (1) to (25), wherein the antibody is a chimeric human antibody, humanized antibody, or human antibody;

(27) a fragment of an antibody according to any one of (1) to (26), wherein the antibody fragment is an antibody fragment selected from F(ab')$_2$, Fab', Fab, single-chain Fv (scFv), disulfide-stabilized Fv (dsFv) or polymers thereof, a dimeric V region (Diabody), and a CDR-containing peptide;

(28) a DNA encoding an antibody or a fragment thereof according to any one of (1) to (27);

(29) a recombinant vector comprising a DNA according to (28);

(30) a transformed cell which is obtained by introducing a recombinant vector according to (29) into a host cell;

(31) a cell which produces an antibody or a fragment thereof according to any one of (1) to (27);

(32) the cell according to (30) or (31), wherein the cell is a hybridoma cell line;

(33) a method for producing an antibody or a fragment thereof according to any one of (1) to (30), characterized by comprising culturing a cell according to any one of (30) to (32) to produce the antibody or the fragment thereof into a culture and extracting the antibody or the fragment thereof from the culture;

(34) a pharmaceutical composition comprising an antibody or a fragment thereof according to any one of (1) to (27) as an active ingredient;

(35) a pharmaceutical composition for prevention or treatment of MK-related disease, comprising an antibody or a fragment thereof according to any one of (1) to (27) as an active ingredient;

(36) the pharmaceutical composition according to (35), wherein the MK-related disease is disease attributed to cell migration;

(37) the pharmaceutical composition according to (36), wherein the disease attributed to cell migration is cancer (or cancer metastasis) or inflammatory disease;

(38) the pharmaceutical composition according to (37), wherein the MK-related disease is autoimmune disease;

(39) the pharmaceutical composition according to (38), wherein the autoimmune disease is multiple sclerosis;

(40) a diagnostic agent for MK-related disease comprising an antibody or a fragment thereof according to any one of (1) to (27); and

(41) a method for screening a substance that binds to an epitope on MK to which an antibody or a fragment thereof according to any one of (1) to (27) binds, comprising the steps of:

(i) bringing MK into contact with a test compound and with an antibody or a fragment thereof according to any one of (1) to (27); and (ii) measuring the binding between the antibody or the fragment thereof according to any one of (1) to (27) and the MK.

Advantages of the Invention

An antibody of the present invention or a fragment thereof inhibits MK functions. Particularly, the antibody of the present invention or the fragment thereof inhibits the cell migration activities of MK.

BEST MODE FOR CARRYING OUT THE INVENTION

Figure 1:
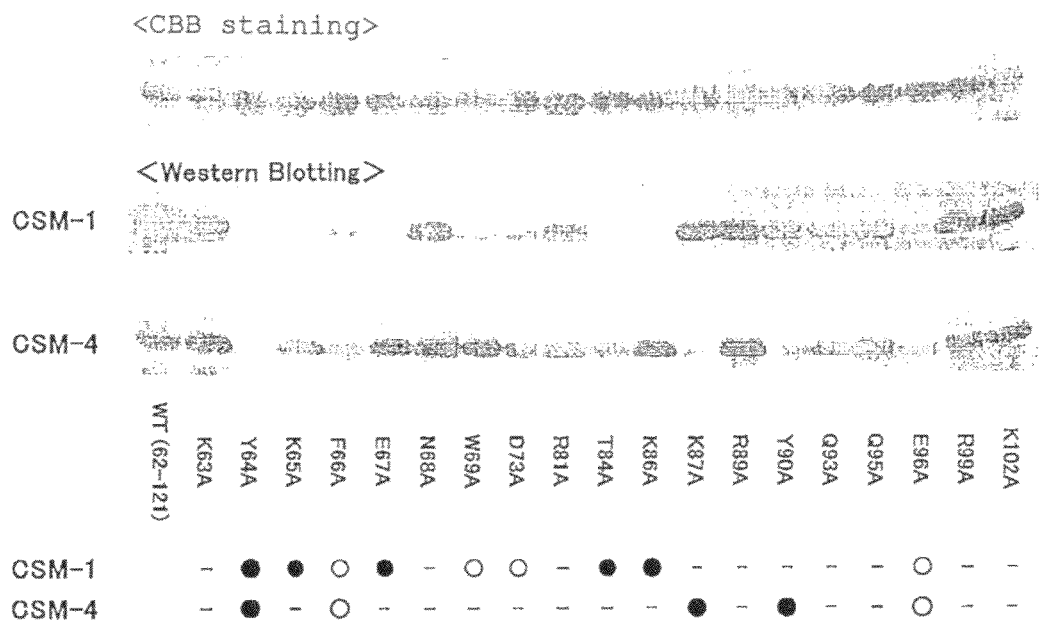
FIG. 1 shows change in antigenicity for CSM-1 and CSM-4 caused by alanine point mutation in an MK C-fragment (MK_62-121). In the diagram, the black circle represents large reduction in antigenicity. The white circle represents reduction in antigenicity. The symbol - represents no change in antigenicity.
Figure 2:
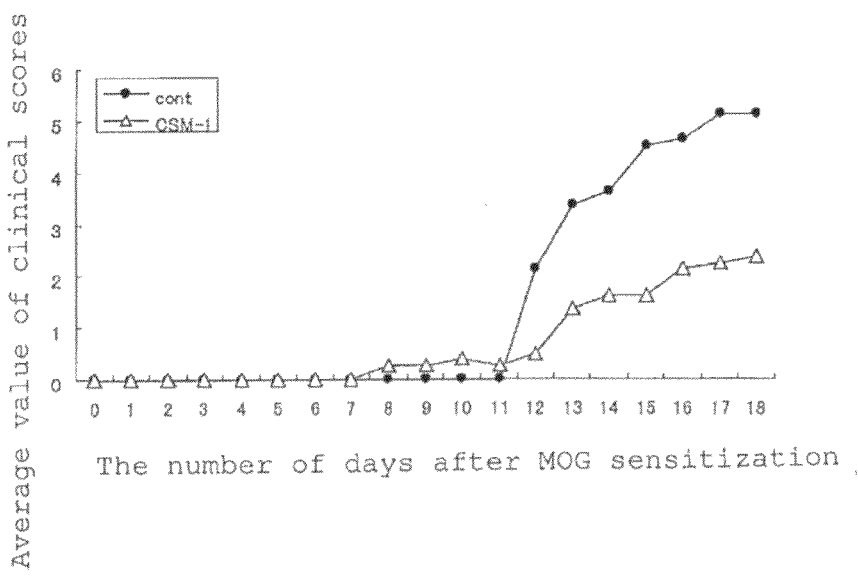
FIG. 2 shows scores of EAE model mice to which CSM-1 has been administered. The ordinate represents an average value of clinical scores of each group. The abscissa represents the number of days after MOG sensitization. Moreover, in the diagram, the black circle represents a control, and the open triangle represents CSM-1-administered mice.

An antibody of the present invention is an antibody that binds to MK and is an antibody or a fragment thereof which recognizes at least a portion of an epitope located at amino acid residues 62 to 104 in the MK amino acid sequence represented by SEQ ID NO: 2 (hereinafter, referred to as a "C-domain-recognizing antibody, etc."). The C-domain-recognizing antibody, etc., of the present invention is preferably an antibody or a fragment thereof which recognizes at least a portion of an epitope located at amino acid residues 64 to 73 and amino acid residues 78 to 101 of MK, an epitope located at amino acid residues 64 to 73, amino acid residues 64 to 69, amino acid residues 64 to 67, or amino acid residues 84 to 96 of MK, an epitope located at amino acid residues 64 to 66 or amino acid residues 87 to 96 of MK, an epitope located at amino acids selected from tyrosine 64, lysine 65, phenylalanine 66, glutamic acid 67, tryptophan 69, aspartic acid 73, threonine 84, lysine 86, and glutamic acid 96 of MK, and an epitope located at amino acids selected from tyrosine 64, phenylalanine 66, lysine 87, tyrosine 90, and glutamic acid 96 of MK.

Moreover, the amino acid residues 64 to 101 in the MK amino acid sequence form the C-domain of MK, which has a three-dimensional structure consisting of three antiparallel β-sheets. The C-domain-recognizing antibody, etc., of the present invention is preferably an antibody or a fragment thereof which recognizes at least a portion of a conformational epitope located at amino acid residues 64 to 73 and amino acid residues 78 to 101 of MK, a conformational epitope located at amino acid residues 64 to 73, amino acid residues 64 to 69, amino acid residues 64 to 67, or amino acid residues 84 to 96 of MK, a conformational epitope located at amino acid residues 64 to 66 or amino acid residues 87 to 96 of MK, a conformational epitope located at amino acids selected from tyrosine 64, lysine 65, phenylalanine 66, glutamic acid 67, tryptophan 69, aspartic acid 73, threonine 84, lysine 86, and glutamic acid 96 of MK, and a conformational epitope located at amino acids selected from tyrosine 64, phenylalanine 66, lysine 87, tyrosine 90, and glutamic acid 96 of MK. The C-domain-recognizing antibody, etc., of the present invention is more preferably an antibody or a fragment thereof which recognizes at least a portion of an antiparallel β-sheet epitope located at amino acid residues 64 to 73 and amino acid residues 78 to 101 of MK, an antiparallel β-sheet epitope located at amino acid residues 64 to 73, amino acid residues 64 to 69, amino acid residues 64 to 67, or amino acid residues 84 to 96 of MK, an antiparallel β-sheet epitope located at amino acid residues 64 to 66 or amino acid residues 87 to 96 of MK, an antiparallel β-sheet epitope located at amino acids selected from tyrosine 64, lysine 65, phenylalanine 66, glutamic acid 67, tryptophan 69, aspartic acid 73, threonine 84, lysine 86, and glutamic acid 96 of MK, and an antiparallel β-sheet epitope located at amino acids selected from tyrosine 64, phenylalanine 66, lysine 87, tyrosine 90, and glutamic acid 96 of MK.

In the present invention, the "conformational epitope" refers to a site to which the antibody binds when amino acids constituting the epitope form a three-dimensional structure identical or analogous to a three-dimensional structure exhibited by the full-length MK protein. For example, among amino acid residues 64 to 73, amino acid residues 78 to 85, and amino acid residues 97 to 101 in the MK amino acid sequence, there exist combinations of amino acids that are located apart from each other on the primary structure but located in proximity to each other on the secondary structure (β-sheet) such that they together form the conformational epitope.

Moreover, in an alternative aspect, the antibody of the present invention or the fragment thereof relates to an antibody or a fragment thereof which recognizes at least a portion of a high electrostatic potential cluster located at amino acid residues 62 to 104 of MK. In this context, the "high electrostatic potential cluster" refers to a site with a positive electrostatic potential in the midkine protein. The electrostatic potential is preferably a potential that exhibits 10 units k_bT/e_c or higher, more preferably 20 units k_bT/e_c or higher, even more preferably 30 units k_bT/e_c or higher, further preferably 40 units k_bT/e_c or higher, most preferably 50 units k_bT/e_c or higher, according to calculation using Pymol. The antibody or the fragment thereof which recognizes at least a portion of a high electrostatic potential cluster located at amino acid residues 62 to 104 of MK is preferably an antibody or a fragment thereof which recognizes at least one amino acid selected from amino acid residues 62 to 64, amino acid residue 66, amino acid residues 68 to 70, amino acid residue 72, amino acid residue 79, amino acid residue 81, amino acid residues 85 to 89, amino acid residue 102, and amino acid residue 103 of MK, more preferably an antibody or a fragment thereof which recognizes at least one amino acid selected from lysine 63, lysine 79, arginine 81, lysine 86, lysine 87, arginine 89, and lysine 102 of MK.

In the present specification, the phrase "recognize at least a portion of" means that the antibody or the fragment recognizes at least one amino acid, preferably at least two amino acids, more preferably at least three amino acids. Moreover, since MK assumes a three-dimensional structure, the epitope and the cluster in the present invention are formed by nonconsecutive amino acids.

Moreover, in an alternative aspect, the antibody of the present invention or the fragment thereof is an antibody or a fragment thereof, wherein CDRs have the amino acid sequence represented by any of SEQ ID NOs: 13 to 24. In the present invention, the "CDR" is as defined by Kabat et al. ("Sequences of Proteins of Immunological Interest", Kabat E. et al., U.S. Department of Health and Human Services, 1983) or Chothia et al. (Chothia & Lesk, J. Mol. Biol., 196, 901-917, 1987). Moreover, in an alternative aspect, the antibody of the present invention or the fragment thereof is an antibody or a fragment thereof, wherein CDRs have a conservatively modified amino acid sequence of the amino acid sequence represented by any of SEQ ID NOs: 13 to 24. In the present invention, the "conservative modification" refers to amino acid modification that neither significantly influences nor significantly alters the binding properties of the antibody containing the amino acid sequence. Examples of such conservative modification can include amino acid substitution, addition, and deletion. The conservative modification can be introduced by a method well known to those skilled in the art (e.g., site-directed mutagenesis and PCR-mediated mutagenesis). When the conservative modification is performed by amino acid substitution, the modification can be achieved by substituting the desired amino acid residue by an amino acid residue similar in side chain thereto. The amino acid residues used in the substitution are not particularly limited as long as it is well known to those skilled in the art that they are similar in side chain. For example, whether or not amino acids are similar in side chain can be determined based on the following side chain properties of amino acids: amino acids having a basic side chain (e.g., lysine, arginine, and histidine), amino acids having an acidic side chain (e.g., aspartic acid and glutamic acid), amino acids having a uncharged polar side chain (e.g., glycine, asparagine, glutamine, serine, threonine, tyrosine, cysteine, and tryptophan), amino acids having a nonpolar side chain (e.g., alanine, valine, leucine, isoleucine, proline, phenylalanine, and methionine), amino acids having a β-branched side chain (e.g., threonine, valine, and isoleucine), and amino acids having an aromatic side chain (e.g., tyrosine, phenylalanine, tryptophan, and histidine).

Furthermore, in an alternative aspect, the antibody of the present invention or the fragment thereof is an antibody or a fragment thereof, wherein CDRs have an amino acid sequence exhibiting 95% or higher homology, preferably 98% or higher homology, more preferably 99% or higher homology, to the amino acid sequence represented by any of SEQ ID NOs: 13 to 24. Moreover, in an alternative aspect, the antibody of the present invention is an antibody or a fragment thereof, wherein CDRs have an amino acid sequence derived from the amino acid sequence represented by any of SEQ ID NOs: 13 to 24 by the deletion, substitution, or addition of one or several amino acids, preferably one or two amino acids, more preferably one amino acid.

In an alternative aspect, the present invention relates to an anti-midkine antibody or a fragment thereof, wherein heavy chain CDR3 has the amino acid sequence represented by SEQ ID NO: 15 or 21, a conservatively modified amino acid sequence thereof, or an amino acid sequence exhibiting 95% or higher homology thereto.

In an alternative aspect, the present invention relates to an anti-midkine antibody or a fragment thereof, wherein heavy chain CDR1 has the amino acid sequence represented by SEQ ID NO: 13, heavy chain CDR2 has the amino acid sequence represented by SEQ ID NO: 14, heavy chain CDR3 has the amino acid sequence represented by SEQ ID NO: 15, light chain CDR1 has the amino acid sequence represented by SEQ ID NO: 16, light chain CDR2 has the amino acid sequence represented by SEQ ID NO: 17, and light chain CDR3 has the amino acid sequence represented by SEQ ID NO: 18. Moreover, in an alternative aspect, the present invention relates to an anti-midkine antibody or a fragment thereof, wherein heavy chain CDR1 has the amino acid sequence represented by SEQ ID NO: 19, heavy chain CDR2 has the amino acid sequence represented by SEQ ID NO: 20, heavy chain CDR3 has the amino acid sequence represented by SEQ ID NO: 21, light chain CDR1 has the amino acid sequence represented by SEQ ID NO: 22, light chain CDR2 has the amino acid sequence represented by SEQ ID NO: 23, and light chain CDR3 has the amino acid sequence represented by SEQ ID NO: 24.

The antibody of the present invention may be an antibody that binds to a substance other than MK as long as it is available as the antibody of the present invention. Preferably, the antibody of the present invention is an antibody that specifically binds to MK. Moreover, a species from which MK recognized by the antibody of the present invention is derived is not particularly limited and is preferably mammalian MK, more preferably mouse, rat, hamster, rabbit, or human MK, even more preferably human MK. The antibody of the present invention may be a polyclonal or monoclonal antibody and is preferably a monoclonal antibody.

Furthermore, the antibody of the present invention encompasses nonhuman animal antibodies, antibodies having a nonhuman animal antibody amino acid sequence and a human-derived antibody amino acid sequence, and human antibodies. Examples of the nonhuman animal antibodies can include mouse, rat, hamster, and rabbit antibodies. The nonhuman animal antibodies are preferably antibodies of animals from which hybridomas can be produced, more preferably mouse antibodies. Examples of the antibodies having a nonhuman animal antibody amino acid sequence and a human-derived antibody amino acid sequence can include: a chimeric human antibody which is obtained by replacing antigen-binding domains Fv in a human antibody by those in an animal-derived monoclonal antibody; and a humanized antibody which is obtained by incorporating, into human antibody frames, CDR sequences on Fv domains directly involved in the antigen binding of an animal-derived antibody monoclonal antibody. Moreover, the human antibodies refer to human antibodies as expression products of antibody genes completely derived from humans.

The present invention also encompasses an anti-MK antibody fragment. In this context, the "antibody fragment" refers to a portion (partial fragment) of an antibody or a peptide containing a portion of an antibody, which maintains the effects of the antibody on antigens. Examples of such an antibody fragment can include F(ab')$_2$, Fab', Fab, single-chain Fv (hereinafter, referred to as "scFv"), disulfide-stabilized Fv (hereinafter, referred to as "dsFv") or polymers thereof, a dimeric V region (hereinafter, referred to as "Diabody"), and a CDR-containing peptide.

The F(ab')$_2$ is an antibody fragment of approximately 100,000 in molecular weight having antigen-binding activities, which is obtained by treating IgG with protease pepsin. The Fab' is an antibody fragment of approximately 50,000 in molecular weight having antigen-binding activities, which is obtained by cleaving the disulfide bond in the hinge region of the F(ab')$_2$. The sdFv is a polypeptide having antigen-binding activities, which comprises one VH and one VL linked via a peptide linker. The dsFv is a fragment having antigen-binding activities, which comprises VH and VL domains containing a cysteine residue substituted for an amino acid residue and has a disulfide bond that links these domains via the cysteine residues. The Diabody is a dimeric fragment of scFvs. The Diabody of the present invention may be monospecific or bispecific (polyspecific antibody). The scFvs in the dimer may be the same or different. The CDR-containing peptide is a peptide containing the amino acid sequence of at least one CDR selected from heavy chain variable region CDR1, CDR2, and CDR3 and light chain variable region CDR1, CDR2, and CDR3.

The number of amino acids recognized by the antibody or the fragment thereof is not particularly limited as long as the antibody can bind to MK and inhibit MK functions. The number of amino acids recognized by the antibody or the fragment thereof is preferably at least one, more preferably at least three.

Moreover, an immunoglobulin class to which the antibody of the present invention belongs is not particularly limited. It may be any immunoglobulin class of IgG, IgM, IgA, IgE, IgD, and IgY and is preferably IgG. Moreover, the antibody of the present invention encompasses even antibodies of any isotype.

The antibody of the present invention inhibits MK functions and can therefore be used as therapeutic and preventive drugs for MK-related disease. In the present invention, the "MK-related disease" refers to a disease involving MK functions. Examples of such a disease can include: diseases attributed to cell growth or angiogenesis, such as cancers (esophageal cancer, thyroid cancer, urinary bladder cancer, colon cancer, stomach cancer, pancreatic cancer, thoracic cancer, liver cancer, lung cancer, breast cancer, neuroblastoma, glioblastoma, uterine cancer, ovarian cancer, prostatic cancer, and Wilms tumor) and endometriosis; inflammatory diseases or diseases attributed to cell migration, such as arthritis, autoimmune disease (organ-specific autoimmune disease, etc.), rheumatic arthritis (rheumatoid arthritis (RA) or osteoarthritis (OA)), multiple sclerosis (relapsing-remitting multiple sclerosis, etc.), inflammatory bowel disease (Crohn disease, etc.), systemic lupus erythematosus (SLE), progressive systematic sclerosis (PSS), Sjogren's syndrome, polymyositis (PM), dermatomyositis (DM), polyarteritis nodosa (PN), thyroid disease (Graves disease, etc.), Guillain-Barre syndrome, primary biliary cirrhosis (PBC), idiopathic thrombocytopenic purpura, autoimmune hemolytic anemia, experimental autoimmune myasthenia gravis (EAMG), amyotrophic lateral sclerosis (ALS), type I diabetes mellitus, transplant rejection, postoperative adhesion, endometriosis, psoriasis, lupus, allergy, asthma, and neutrophil dysfunction; and occlusive vascular diseases or diseases attributed to vascular intimal thickening, such as post-revascularization restenosis, coronary occlusive disease, cerebrovascular occlusive disease, renovascular occlusive disease, peripheral occlusive disease, arteriosclerosis, and cerebral infarction. The MK-related disease of the present invention is preferably cancer, arteriosclerosis, angiogenesis-related disease, angina pectoris, myocardial infarction, cerebral infarction, cerebral hemorrhage, hypertension, or multiple sclerosis.

The antibody of the present invention can be used as a diagnostic agent for MK-related disease. When the antibody of the present invention is used as a diagnostic agent, the antibody used or a fragment thereof is preferably an antibody or a fragment thereof that specifically recognizes MK.

1. Preparation of Anti-MK Antibody

The antibody of the present invention can be prepared, for example, by immunizing nonhuman mammals or birds with MK or with peptide(s) having a portion of MK such as a peptide having an amino acid sequence contained at residues 64 to 104 of MK, a peptide having an amino acid sequence contained at residues 64 to 73 of MK, a peptide having an amino acid sequence contained at residues 64 to 69 of MK, a peptide having an amino acid sequence contained at residues 64 to 67 of MK, a peptide having an amino acid sequence contained at residues 64 to 66 of MK, a peptide having an amino acid sequence contained at residues 78 to 101 of MK, a peptide having an amino acid sequence contained at residues 84 to 96 of MK, and/or a peptide having an amino acid sequence contained at residues 87 to 96 of MK (hereinafter, referred to as "peptides having a portion of MK"), if necessary together with an immunostimulant (e.g., mineral oil or aluminum precipitates with heat-killed bacterium or lipopolysaccharide, a complete Freund's adjuvant, or an incomplete Freund's adjuvant). The antibody of the present invention can be prepared, preferably, by immunizing MK-knockout mice with MK (see Japanese Patent Laid-Open No. 2002-85058 and Nakamura, E. et al.: Genes Cells 3, p. 811-822).

The MK used as an immunogen is not particularly limited as long as it is mammalian MK. The MK is preferably human MK. For example, mouse, rabbit, or human MK has already been cloned, and the sequence of human MK has been reported (SEQ ID NO: 1) (see Japanese Patent Laid-Open No. 5-91880 and Tsutui, J. et al.: Biochem. Biophys. Res. Commun. 176, p. 792-797). Thus, the immunogen used in the preparation of the antibody of the present invention can be obtained by introducing an expression vector containing MK-encoding cDNA into *E. coli*, yeast, insect cells, animal cells, or the like for gene expression. For example, MK-encoding DNA is incorporated into an expression vector, which is in turn introduced into *Pichia* yeast for gene expression, and the expressed protein can be collected from a culture supernatant of the yeast and prepared as recombinant MK (see Japanese Patent Laid-Open No. 9-95454).

When the peptides having a portion of MK are used as immunogens, the immunogens can be obtained by introducing expression vectors containing cDNAs encoding these peptides into *E. coli*, yeast, insect cells, animal cells, or the like for gene expression.

When the peptides having a portion of MK are used as immunogens, the peptides having a portion of MK can be used directly. The peptides having a portion of MK can be used alone or as a conjugate of two or more thereof linked via a linker. For example, the peptides having a portion of MK such as the C-fragment of MK (peptide having an amino acid sequence at residues 62 to 121 of MK) and a peptide having an amino acid sequence at residues 64 to 101 of MK can be used directly. Alternatively, a peptide having an amino acid sequence at residues 64 to 73 of MK and a peptide having an amino acid sequence at residues 78 to 101 of MK can be used as a conjugate linked via a linker.

The MK or the peptides having a portion of MK can be prepared by chemical synthesis using an Fmoc method, Boc method, or the like. For example, the C-terminal amino acid of the MK or the peptides having a portion of MK is immobilized on a polystyrene carrier, and steps involving the binding of an amino acid protected with a 9-fluorenylmethyloxycarbonyl (Fmoc) or tert-butoxycarbonyl (Boc) group thereto through reaction using a condensing agent such as diisopropylcarbodiimide (DIC), washing, and deprotection can be repeated to obtain a peptide having the desired amino acid sequence.

Moreover, the MK or the peptides having a portion of MK can also be synthesized using an automatic peptide synthesizer. Examples of such a peptide synthesizer include: PSSM-8 (Shimadzu Corp.); Model 433A peptide synthesizer (Applied Biosystems, Inc.); and ACT 396 Apex (Advanced ChemTech Inc.). Alternatively, the MK can also be synthesized according to a previously reported method (Inui, T. et al.: J. Peptide Sci., 2: p. 28-39, 1996).

The immunized animals are not particularly limited as long as they are animals from which hybridomas can be produced, such as mice, rats, hamsters, rabbits, chickens, and ducks. The immunized animals are preferably mice or rats, more preferably mice, most preferably MK-knockout mice.

The immunogen can be administered to the animals, for example, by hypodermic injection, intraperitoneal injection, intravenous injection, intradermal injection, intramuscular injection, or footpad injection and is preferably administered by hypodermic injection or intraperitoneal injection. The amount of the immunogen used is not particularly limited as long as it is an amount that permits antibody production. The amount is preferably 0.1 to 1000 μg, more preferably 1 to 500 μg, even more preferably 10 to 100 μg. The immunization can be performed once or several times at appropriate intervals.

Preferably a total of 2 to 5 once-a-week to every-five-week immunizations, more preferably a total of 3 every-three-week immunizations, are performed. One to two weeks after the final immunization, blood is collected from the orbits or tail veins of the immunized animals, and antibody titers are measured using the sera. The antibody titer measurement can be conducted by a method well known to those skilled in the art. Examples thereof can include radioimmunoassay (RIA), enzyme-linked immunosorbent assay (ELISA), fluorescent antibody technique, and passive hemagglutination. The method is preferably ELISA. The antibody of the present invention can be obtained by purification from animal sera that exhibit a sufficient antibody titer.

The monoclonal antibody of the present invention can be obtained by culturing hybridomas which are obtained by fusing myeloma cells with antibody-producing cells obtained from the immunologically sensitized animals immunized by the method described above. Examples of the fusion method can include the method of Milstein et al. (Galfre, G. & Milstein, C., Methods Enzymol. 73: 3-46, 1981).

The antibody-producing cells used can be collected from the spleen, pancreas, lymph node, or peripheral blood of the mice or rat immunized by the method described above whose sera exhibit a sufficient antibody titer, and are preferably collected from the spleen thereof.

The myeloma cells used are not particularly limited as long as they are cells derived from mammals such as mice, rat, guinea pigs, hamsters, rabbits, or humans and can grow in vitro. Examples of such cells can include P3-X63Ag8 (X63) (Nature, 256, 495, 1975), P3/NS1/1-Ag4-1 (NS1) (Eur. J. Immunol., 6, 292, 1976), P3X63Ag8U1 (P3U1) (Curr. Top. Microbiol. Immunol., 81, 1, 1978), P3X63Ag8. 653 (653) (J. Immunol., 123, 1548, 1979), Sp2/0-Ag14 (Sp2/O) (Nature, 276, 269, 1978), Sp2/O/FO-2 (FO-2) (J. Immunol. Methods, 35, 1, 1980), the cells are preferably P3U1.

The antibody-producing cells obtained according to the method described above and the myeloma cells are washed with a medium, PBS (phosphate buffered saline), or the like and then cell-fused by the addition of a cell-aggregating medium such as polyethylene glycol (hereinafter, referred to as "PEG") (Elsevier Publishing, 1988). The ratio between the antibody-producing cells and the myeloma cells for fusion is, for example, 2:1 to 1:2. After cell fusion, the fused cells are cultured in a medium such as a HAT (hypoxanthine-aminopterin-thymidine) medium for selective growth of hybridomas. After culture, the culture supernatant is collected, and samples that bind to antigenic proteins but do not bind to nonantigenic proteins are selected by ELISA or the like. The samples are prepared as single cells by limiting dilution, from which cells that stably exhibit a high antibody titer are in turn selected.

The monoclonal antibody of the present invention can be obtained by culturing in vitro the hybridomas obtained by the method described above and purifying antibodies from the culture solution. Alternatively, the monoclonal antibody of the present invention can also be obtained by: transplanting the hybridomas into syngeneic or immunodeficient animals to which pristane has been administered intraperitoneally in advance; then collecting ascitic fluids from the animals; and purifying antibodies from the collected ascitic fluids.

The monoclonal antibody purification can be performed by collecting, after centrifugation, an IgG fraction using a protein A column, protein G column, or the like. When the monoclonal antibody belongs to an antibody class of IgY or IgM, it can be purified using a column with mercaptopyridine as a ligand. Alternatively, the purification can also be performed using an MK-immobilized column, ion-exchange chromatography, hydrophobic interaction chromatography, or the like, irrespective of antibody classes.

2. Preparation of Chimeric Human Antibody, Humanized Antibody, and Human Antibody (1) Chimeric Human Antibody The chimeric human antibody of the present invention can be obtained by: separately preparing DNAs encoding VH and VL of a nonhuman animal-derived monoclonal antibody that binds to MK and inhibits MK functions; binding them to human-derived immunoglobulin constant region cDNAs; incorporating the constructs into expression vectors; and introducing the vectors into appropriate hosts for gene expression (Morrison, S. L. et al., Proc. Natl. Acad. Sci. USA, 81, 6851-6855, 1984).

The DNAs encoding VH and VL of a nonhuman animal-derived monoclonal antibody can be obtained, for example, by the following method: mRNAs are extracted from B cells of animals that produce the monoclonal antibody. The mRNA extraction can be performed by a method well known to those skilled in the art. For example, RNAs are prepared by a guanidine-ultracentrifugation method (Chirgwin, J. M. et al., Biochemistry, 18, 5294-5299, 1979), an AGPC method (Chomczynski, P et al., Analytical Biochemistry, 162, 156-159, 1987), or the like, and mRNAs can then be purified therefrom using an mRNA purification kit (manufactured by Amersham Pharmacia Biotech, Inc. or TAKARABIO INC.) or the like. cDNAs are prepared from the extracted mRNAs using oligo dT primers and incorporated into vectors. From among the cDNAs incorporated in vectors, cDNAs encoding the nonhuman animal-derived monoclonal antibody are isolated using a portion of the nonhuman animal-derived monoclonal antibody gene as a probe. The isolated cDNAs can be sequenced to obtain the VH- and VL-encoding DNA sequences of interest.

Moreover, another method for obtaining the DNAs encoding VH and VL of a nonhuman animal-derived monoclonal antibody includes the following method: the VH or VL genes are amplified by: amplifying the thus-obtained cDNAs by PCR using primers capable of amplifying VH or VL genes (e.g., primers hybridizing to a mouse H chain constant region (C region) gene and primers hybridizing to the conserved sequence of a mouse L chain constant region when mice are used as the nonhuman animals (R. Orlandi et al., Proc. Natl. Acad. Sci. USA, 86, 3833, 1989)); or extracting mRNAs from B cells of animals that produce the monoclonal antibody, followed by RT-PCR using the primers capable of amplifying VH or VL genes. The DNA fragments of interest are extracted from the obtained PCR products. The extraction of the DNA fragments of interest can be performed, for example, by excising, after agarose gel electrophoresis, bands that exhibit a DNA size of interest and extracting DNAs from the gel slices. The vectors and the extracted DNAs are treated with restriction enzymes. Then, the extracted DNAs are incorporated into the vectors, and the incorporated DNAs can be sequenced to obtain the VH- and VL-encoding DNA sequences of interest.

Arbitrary human antibody CH and CL can be used as the human antibody CH and CL for the chimeric human antibody. Examples thereof can include human γ1 or γ2 CH and human κ CL. Chromosomal DNAs or cDNAs can be used as the genes encoding human antibody CH and CL. For example, the DNAs encoding VH and VL of a nonhuman animal-derived monoclonal antibody obtained by the method described above can be bound with the DNAs encoding human antibody CH and CL, respectively, and the constructs can be incorporated into expression vectors for animal cells to prepare vectors for expression of the chimeric antibody of the present invention.

Examples of an enhancer and a promoter used in the expression of the chimeric human antibody can include an enhancer and a promoter of an immunoglobulin gene itself or a nonimmunoglobulin enhancer and promoter. For example, when mice are used as the nonhuman animals, the recombinant DNAs can also be prepared in the form comprising a mouse or human enhancer sequence present between J and C genes because the expression regulation mechanisms of immunoglobulin genes are common between mice and humans.

For example, pSV2-gpt (R. C. Mulligan and P. Berg, Science, 209, 1422, 1980) can be used as the expression vectors for animal cells. The genes encoding H and L chains of the chimeric human antibody of the present invention prepared by the method described above may be incorporated in the same vector or different vectors.

(2) Humanized Antibody

The humanized antibody of the present invention can be obtained by: separately constructing DNAs encoding V regions comprising VH and VL CDR amino acid sequences of a nonhuman animal-derived monoclonal antibody that binds to MK and inhibits the cell migration activities of MK, which are grafted onto human antibody VH and VL FRs, respectively; binding the constructed DNAs to human-derived immunoglobulin constant region cDNAs; and incorporating the constructs into expression vectors, which are in turn introduced into appropriate host cells for gene expression (see L. Rieohmann et al., Nature, 332, 323, 1988; Kettleborough, C. A. et al., Protein Eng., 4, 773-783, 1991; and Clark M., Immunol. Today., 21, 397-402, 2000).

The CDR amino acid sequences of a nonhuman animal-derived monoclonal antibody can respectively be obtained by comparing amino acid sequences predicted from the DNA sequences encoding VH and VL of a nonhuman animal-derived monoclonal antibody obtained by the method described above to the full amino acid sequences of VH and VL of a known antibody. The amino acid sequences of a known antibody can be obtained, for example, from antibody amino acid sequences registered in a database such as Protein Data Bank. The CDR amino acid sequences are preferably amino acid sequences represented by SEQ ID NOs: 13 to 24, conservatively modified amino acid sequences thereof, or amino acid sequences exhibiting 95% or higher homology thereto.

Moreover, the human antibody FRs are not particularly limited as long as antibodies after grafting exert the effects of the present invention. The human antibody FRs are preferably human antibody FRs that provide a humanized antibody whose V regions are analogous in three-dimensional structure to the V regions of the nonhuman animal-derived monoclonal antibody or human antibody FRs that have high amino acid sequence homology to the FRs of the nonhuman animal-derived monoclonal antibody used. Whether or not the selected human antibody FRs provide a humanized antibody whose V regions are analogous in three-dimensional structure to the V regions of the nonhuman animal-derived monoclonal antibody can be determined, for example, by predicting three-dimensional structures by computer modeling based on DNA sequence information about the V regions containing the selected human antibody FRs and comparing the three-dimensional structures to the three-dimensional structures of the V regions of the nonhuman animal-derived monoclonal antibody used. The FR amino acid sequences of the nonhuman animal-derived monoclonal antibody used can be obtained from information about the amino acid sequences predicted from the VH- and VL-encoding DNA sequences obtained by the method described above and the CDR amino acid sequences. Moreover, for obtaining the human antibody FRs that provide a humanized antibody whose V regions are analogous in three-dimensional structure to the V regions of the nonhuman animal-derived monoclonal antibody or the human antibody FRs that have high amino acid sequence homology to the FRs of the nonhuman animal-derived monoclonal antibody used, the amino acid sequences of the obtained human antibody FRs can be mutagenized appropriately.

The humanized antibody V region-encoding DNA sequences used are designed as DNA sequences corresponding to amino acid sequences comprising CDR amino acid sequences of a nonhuman animal-derived monoclonal antibody bound with human antibody FR amino acid sequences. The humanized antibody V region-encoding DNAs can be prepared by a method well known to those skilled in the art based on the designed DNA sequences. For example, based on the designed DNAs, DNA fragments of around 100 by in length can be synthesized chemically as synthetic DNAs and amplified by PCR to obtain the DNA sequences of interest. Moreover, the DNA fragments of around 100 by are bound using an enzyme such as ligase and subjected to PCR using primers encoding both terminal sequences of the designed humanized antibody V region-encoding DNA sequences, and DNA fragments with the desired length can be extracted to obtain the DNA fragments of interest. Furthermore, the humanized antibody V region-encoding DNA used in PCR can also be obtained by a method known as CDR grafting. Moreover, the humanized antibody V region-encoding DNAs used can also be obtained by incorporating CDR-encoding DNAs into human antibody V region DNAs through site-directed mutagenesis. The site-directed mutagenesis can be performed using, for example, Gene Tailor Site-Directed Mutagenesis System (Invitrogen Corp.), Transformer Site-Directed Mutagenesis Kit (Clontech), or Site-Directed Mutagenesis System (TAKARABIO INC.) according to the instruction included in the kit.

Arbitrary human antibody CH and CL can be used as the human antibody CH and CL for the humanized antibody. Examples thereof can include human γ1 or γ2 CH and human κ CL. Chromosomal DNAs or cDNAs can be used as the genes encoding human antibody CH and CL. For example, the humanized antibody V region-encoding DNAs obtained by the method described above can be bound with the DNAs encoding human CH and CL, respectively, and the constructs can be incorporated into expression vectors for animal cells to prepare vectors for expression of the humanized antibody of the present invention.

Examples of an enhancer and a promoter used in the expression of the humanized antibody can include an enhancer and a promoter of an immunoglobulin gene itself or a nonimmunoglobulin enhancer and promoter. For example, when mice are used as the nonhuman animals, the recombinant DNAs can also be prepared in the form comprising a mouse or human enhancer sequence present between J and C genes because the expression regulation mechanisms of immunoglobulin genes are common between mice and humans.

For example, pSV2-gpt (R. C. Mulligan and P. Berg, Science, 209, 1422, 1980) can be used as the expression vectors for animal cells. The genes encoding H and L chains of the humanized antibody of the present invention prepared by the method described above may be incorporated in the same vector or different vectors.

In this context, the nonhuman animal-derived monoclonal antibody used in the preparation of the chimeric human antibody or the humanized antibody is not particularly limited as long as it is an antibody that binds to MK and inhibits the cell migration activities of MK. The nonhuman animal-derived monoclonal antibody is preferably a mouse monoclonal antibody.

(3) Human Antibody

The human antibody can be obtained using, for example, a human antibody phage library or human antibody-producing transgenic mice (Tomizuka et al., Nature Genet., 15, 146-156 (1997)).

The human antibody phage library is a phage library which is obtained by introducing, into phage genes, VH and VL genes from an antibody gene pool having various human B cell-derived sequences such that human antibody Fab or scFv or the like is displayed as fusion proteins on the phage surface. Examples of such a human antibody phage library can include: a naive (nonimmune) library (Cambridge Antibody Technology, Medical Research Council, Dyax Corp., etc.) which is obtained by amplifying VH and VL genes of a normal human antibody by RT-PCR from peripheral lymphocytes or the like and creating a library; a synthetic library (BioInvent, Crucell, and Morphosys AG) which is obtained by selecting particular functional antibody genes within human B cells, substituting particular sites of antigen-binding region (e.g., CDR3 region) genes in V gene fragments by oligonucleotides encoding random amino acid sequences with an appropriate length, and creating a library; and an immune library which is a library prepared from the lymphocytes of patients with cancer, autoimmune disease, or infectious disease, or humans vaccinated with the target antigen.

For example, the naive human antibody phage library can be prepared by the following method: mRNAs are prepared from human peripheral blood, and cDNAs of V genes are synthesized separately using primers specific for immunoglobulin γ-, μ-, κ-, and λ-constant regions. Each V gene is synthesized using a DNA primer set specific for the V gene family, and these synthesized genes are linked by PCR using linker DNA encoding a linker peptide such as (Gly4Ser)$_3$ to synthesize scFv genes. The synthesized scFv genes are inserted into phagemid vectors such as pCANTAb5E using both terminal restriction sites for facilitating gene introduction into the vectors. *E. coli* is transformed with the vectors and subjected to rescue using helper phages.

When the human antibody phage library is used, for example, the target MK immobilized on a solid phase is reacted with the phage antibody library, and unbound phages can be removed by washing, followed by collection of bound phages to obtain the desired clones (panning). Moreover, the obtained phages are amplified, and panning can be repeated for the amplified library to thereby enhance the precision of the obtained clones. The VH and VL genes of the obtained clones can also be analyzed to thereby prepare a complete human antibody having these gene sequences.

The human antibody-producing transgenic mice are mice which are obtained by introducing human antibody immunoglobulin (Ig) genes into endogenous Ig gene-knockout mice. The human antibody-producing transgenic mice can be obtained, for example, by the following method: human-mouse hybrid cells are treated with colcemid (spindle formation inhibitor) for 48 hours to form microcells, constructs comprising one to several chromosomes enveloped by a nuclear membrane. The microcells isolated in the presence of cytochalasin B are fused to recipient cells (mouse ES cells) for chromosome transfer using polyethylene glycol to prepare microcell-hybrid ES cells, which are in turn injected into mouse embryos.

The human antibody-producing transgenic mice can be used as the immunized animals and immunized with antigens according to the method for anti-MK antibody preparation described above to obtain an anti-MK human antibody.

3. Preparation of Antibody Fragment

The fragment of the antibody of the present invention (F(ab')$_2$, Fab', Fab, scFv, dsFv or polymers thereof, Diabody, or a CDR-containing peptide) can be prepared according to methods shown below.

The F(ab')$_2$ fragment of the present invention can be obtained as an antibody fragment of approximately 100,000 in molecular weight having antigen-binding activities, by cleaving the H chain of the MK-binding IgG antibody of the present invention at amino acid residue 234 by treatment with protease pepsin. Alternatively, the F(ab')$_2$ fragment of the present invention can be obtained by binding Fab' fragments described later through a thioether or disulfide bond.

The Fab' fragment of the present invention can be obtained by treating the MK-binding F(ab')$_2$ of the present invention thus obtained with a reducing agent dithiothreitol. Alternatively, the Fab' fragment of the present invention can be obtained by inserting DNA encoding Fab' of the MK-binding antibody of the present invention into expression vectors, which are in turn introduced into host cells for gene expression.

The Fab fragment of the present invention can be obtained as an antibody fragment of approximately 50,000 in molecular weight having antigen-binding activities, by cleaving the H chain of the MK-binding antibody of the present invention at amino acid residue 224 by treatment with protease papain such that about N-terminal half of the H chain and the whole region of the L chain are bound through a disulfide bond. Alternatively, the Fab fragment of the present invention can be obtained by inserting DNA encoding Fab of the MK-binding antibody of the present invention into expression vectors, which are in turn introduced into host cells for gene expression.

The scFv of the present invention can be obtained by: separately obtaining cDNAs encoding VH and VL of the MK-binding antibody of the present invention; inserting linker sequence-encoding DNA into between these genes to construct scFv-encoding DNA; and inserting the DNA into expression vectors, which are in turn introduced into host cells for gene expression. The length of the linker is not particularly limited as long as it is a length that permits the association of VH and VL. The length is preferably 10 to 20 residues, more preferably 15 residues. Moreover, the linker sequence is not particularly limited as long as it does not inhibit the folding of the polypeptide chains of two domains, VH and VL. The linker sequence is preferably a linker consisting of glycine and/or serine, more preferably GGGGS (G: glycine and S: serine) or a repeated sequence thereof.

The dsFv of the present invention can be obtained by substituting one amino acid residue in each of VH and VL by a cysteine residue through site-directed mutagenesis and binding these VH and VL regions through a disulfide bond between the cysteine residues. The substituted amino acid is not particularly limited as long as it is an amino acid residue that has no influence on antigen binding based on the three-dimensional structure.

The Diabody of the present invention can be obtained by constructing the scFv-encoding DNA such that a linker has an amino acid sequence of 8 or less residues (preferably 5 residues) and inserting the DNA into expression vectors, which are in turn introduced into host cells for gene expression. Bispecific Diabody can be obtained by combining VH and VL DNAs of two different scFvs to prepare ScFv.

The CDR-containing peptide of the present invention can be obtained by constructing DNA encoding a VH or VL CDR amino acid sequence of the MK-binding antibody of the present invention and inserting the DNA into expression vectors, which are in turn introduced into host cells for gene expression.

4. Selection of C-Domain-Recognizing Antibody, Etc.

The C-domain-recognizing antibody, etc. of the present invention can be obtained by selecting antibodies or the like that recognize the desired epitope from among the antibodies or the fragments thereof obtained by the methods described above. Moreover, the C-domain-recognizing antibody of the present invention can be obtained according to the method for anti-MK antibody preparation described above by administering peptides having the desired epitope sequence as antigens.

Whether or not the obtained antibodies recognize an epitope recognized by the antibody of the present invention can be determined by a method well known to those skilled in the art. For example, alanine mutation is introduced into amino acid sequences recognized by the C-domain-recognizing antibody, etc. of the present invention among amino acids constituting MK to prepare alanine mutants of full-length MK or MK fragments, and binding activities thereof with the obtained antibodies are measured. Antibodies that are weakly bound with the alanine mutants of full-length MK or MK fragments can be selected to obtain the antibody of the present invention.

The binding between the obtained antibodies and the alanine mutation-introduced MK can be measured by a method well known to those skilled in the art. Examples of such a method can include western blotting, X-ray crystallographic analysis, and Biacore System (Biacore).

5. Pharmaceutical Composition

When the antibody of the present invention is used as a pharmaceutical agent, examples of administration routes can include oral administration, intraoral administration, intratracheal administration, hypodermic administration, intramuscular administration, and intravascular (intravenous) administration. Moreover, examples of preparations can include injections, capsules, tablets, syrups, granules, patches, and ointments. The antibody of the present invention may be administered alone or in combination with a pharmacologically acceptable carrier (see "Pharmaceutical Excipient Dictionary" Yakuji Nippo Ltd. and "Handbook of Pharmaceutical Excipients" APhA Publications).

6. Diagnostic Agent

The diagnostic agent of the present invention can be based on a method known in the art using antibody molecules. Examples of such a method can include ELISA (Catty, Raykundalia, 1989), radioimmunoassay (Catty, Murphy, 1989), immunohistological method (Heider et al., 1993), and western blotting. For example, tissue samples or liquids collected as biopsies from test subjects can be used as specimens for the diagnostic agent of the present invention. The biopsies used are not particularly limited as long as they are targeted by the immunological measurement of MK. Examples thereof can include tissues, blood, urine, serous fluids, spinal fluids, synovial fluids, aqueous humor, lacrimal fluids, saliva or frac-tionated or processed products thereof. Analysis using the diagnostic agent of the present invention can be conducted qualitatively, quantitatively, or semi-quantitatively.

Hereinafter, the present invention will be described more specifically with reference to Examples. However, the present invention is not intended to be limited to these Examples.

Example 1

Preparation of Mouse Anti-Human MK Monoclonal Antibodies

1. Preparation of MK Gene-Knockout Mice

MK gene-knockout mice were prepared by a method known in the art (Japanese Patent Laid-Open No. 2002-85058 and Nakamura, E. et al.: Genes Cells 3, p. 811-822).

2. Preparation of Mouse Anti-Human MK Monoclonal Antibodies 2-1. Preparation of Antigens Human MK mRNAs were prepared from a cultured cell line G-401 derived from Wilms tumor (Tsutsui, J. et al., Biochem. Biophys. Res. Commun. 176, 792-797, 1991). Primers were designed such that they contained a sequence recognized by a restriction enzyme EcoRI (5'-GAATTC-3'). PCR (polymerase chain reaction) of 30 cycles each involving temperature change of 93° C.→37° C.→72° C. was performed using sense PCR primer: 5'-GCGGAATTCATG-CAGCACCGAGGCTTCCTC-3' (SEQ ID No: 3), and anti-sense PCR primer: 5'-GCGGAATTCCTAGTCCTTTCCCTTCCCTTT-3' (SEQ ID No: 4) and the human MK mRNAs as templates to prepare human MK cDNAs comprising the MK coding region flanked by EcoRI restriction sites.

The MK cDNAs and expression vectors pHIL301 (containing histidine and a neomycin resistance gene; see Japanese Patent Laid-Open No. 2-104292 and EP Patent No. 0339568) for yeast *Pichia pastoris* GS115 (hereinafter, referred to as "*Pichia* yeast GS115") were digested with a restriction enzyme EcoRI and then ligated using a ligation kit (manufactured by TAKARABIO INC.) to prepare recombinant expression vectors.

The recombinant expression vectors thus prepared were introduced into *Pichia* yeast GS115 (manufactured by Invitrogen Corp.) using electroporation. The vector-introduced *Pichia* yeast GS115 was cultured in a G418-containing medium free from histidine to obtain several clones having the MK gene of interest. The obtained clones were cultured, while induced with methanol. The culture supernatant was collected, and western blotting using rabbit anti-mouse MK polyclonal antibodies was conducted to confirm whether the clones secreted MK.

One of the clones that secreted MK into the culture supernatant by the induction was designated as T3L-50-4P, and this clone was cultured (see Japanese Patent Laid-Open No. 7-39889). The MK secretion products were collected from the culture supernatant and subjected to purification by ion-exchange chromatography and affinity chromatography using a heparin column to obtain highly pure MK.

2-2. Immunization

The MK-knockout mice were immunized with the antigens. The antigens were prepared as an antigen solution in an amount of 10 µg per mouse diluted with a saline to 0.1 ml, and mixed with 0.1 ml of FCA for emulsification, and this mixture was hypodermically administered to the dorsal regions of the mice. The mice were immunized on a total of 8 occasions, two weeks apart. The 8th immunization was performed by administering a solution containing 10 µg of the antigen solution directly dissolved in 0.1 ml of a saline to the tail veins of the mice through intravenous injection.

On day 6 after the 4th immunization and day 8 after the 6th immunization, sera collected from the eyegrounds of the mice were used to examine serum antibody titers by ELISA.

The ELISA was conducted by the following method: first, the antigen solution was prepared to a concentration of 1.0 μg/ml or 0.1 μg/ml with PBS (pH 7.2 to 7.4) and dispensed in an amount of 50 μl/well or 100 μl/well to a 96-well assay plate (manufactured by BD FALCON, 353912; or manufactured by NUNC, 468667), which was then left standing overnight at 4° C. to immobilize the antigens thereon. The plate was washed three times with 0.05% Tween 20-PBS. Then, 4-fold-diluted BlockAce (manufactured by Dainippon Pharmaceutical Co., Ltd.) in an amount of 100 μl/well or 1% BSA (manufactured by Wako Pure Chemical Industries, Ltd., 014-15134)-0.05% Tween 20-PBS in an amount of 300 μl/well was added thereto, and the plate was left standing at 37° C. for 2 hours or overnight at 4° C. for blocking. The plate was washed three times with 0.05% Tween 20-PBS. Then, an undiluted solution of the culture supernatant in an amount of 50 μl/well or 1 μg/ml purified antibodies in an amount of 100 μl/well was added thereto, and the plate was left standing at 37° C. or room temperature for 1 hour. The plate was washed three times with 0.05% Tween 20-PBS. Then, goat anti-mouse IgG+IgM HRP conjugates (manufactured by BIO-SOUCE, AMI3704) diluted 10000-fold with 10-fold-diluted BlockAce (added in an amount of 50 μl/well) or peroxidase-conjugated rabbit anti-mouse IgG (H+L) (manufactured by PIERGE, 31452) diluted 10000-fold with 1% BSA-0.05% Tween-PBS (added in an amount of 100 μl/well) were added thereto as secondary antibodies, and the plate was left standing at 37° C. or room temperature for 1 hour. The plate was washed three times with 0.05% Tween 20-PBS. Then, HRP substrates (25 ml of a substrate solution (10.206 mg/ml citric acid monohydrate and 36.82 mg/ml disodium hydrogen phosphate dodecahydrate in distilled $H_2O$), 10 mg of OPD, and 5 μl of 30% $H_2O_2$) in an amount of 50 μl/well or TMB+ Substrate Chromogen (manufactured by DAKO, S1599) in an amount of 100 μl/well were added thereto, and the plate was left standing at room temperature for 20 minutes under shading conditions. The reaction was terminated by the addition of 1 N sulfuric acid in an amount of 50 μl/well, and the antibody titers were measured at a wavelength of 492 nm or 450 nm.

Sufficient antibody titers were obtained in ELISA on day 8 after 6 immunizations. Therefore, three days after the additional two immunizations, cell fusion was performed.

2-3. Cell Fusion

The mice were secured, and their chests were wiped with alcohol-moistened cotton. Blood was collected from the heart using a 2.5 ml syringe and a 23-G needle. After blood collection, the mice were placed in a beaker containing 20 ml of alcohol for disinfection for approximately 3 minutes. The collected blood was placed in a 1.5-ml tube and left at 37° C. for 1 hour and then overnight at 4° C., followed by centrifugation at 3,000 rpm for 10 minutes. The sera were transferred to another 1.5-ml tube and stored at 4° C. after addition of 0.05% sodium azide.

The mice after blood collection were denuded of epithelium using scissors and tweezers. Furthermore, the endothelium was picked up and incised for separation of the spleen. The spleen was washed five times in order with 200 ml of an RPMI1640 S.P medium dispensed in advance to five Petri dishes. The spleen thus washed was placed in a mesh, incised several times with scissors, and crushed using a glass rod. The mesh was washed with an RPMI1640 S.P medium to collect the spleen cells into a 40-ml glass centrifuge. The collected spleen cells were centrifuged at 1200 rpm for 10 minutes, and the supernatant was removed using a suction pipette. 40 ml of an RPMI1640 S.P medium was added to the cells, and the cells were centrifuged at 1200 rpm for 10 minutes. 40 ml of an RPMI1640 S.P medium was added to the obtained spleen cells, and the cells were well stirred. The cell count was measured using a hemocytometer.

Myeloma cells (P3U1) placed in a Petri dish were collected into a 50-ml centrifuge by spraying several times using a pipette. The cells were centrifuged at 1000 rpm for 5 minutes, and the supernatant was removed using a suction pipette. 40 ml of an RPMI1640 S.P medium was added to the cells, and the cells were centrifuged at 1000 rpm for 5 minutes. 40 ml of an RPMI1640 S.P medium was added to the obtained myeloma cells, and the cells were well stirred. The cell count was measured using a hemocytometer.

Based on the results of the cell count measurement, the myeloma cells were placed in the 50-ml glass centrifuge containing the spleen cells such that the ratio between the spleen cells and the myeloma cells was 5:1. After mixing, the cells were centrifuged at 1200 rpm for 10 minutes, and the supernatant was removed using a suction pipette. The centrifuge was then tapped. After tapping, 1 ml of PEG (polyethylene glycol) was gradually added thereto over 1 minute with stirring and directly mixed for 2 minutes. After PEG mixing, 1 ml of an RPMI1640 S.P medium heated in advance to 37° C. in a water bath was gradually added thereto over 1 minute with stirring. This procedure was repeated three times. Then, 10 ml of an RPMI1640 S.P medium heated in advance to 37° C. was gradually added thereto over 3 minutes with stirring. After medium addition, the mixture was heated at 37° C. for 5 minutes in a 5% $CO_2$ incubator and then centrifuged at 1,000 rpm for 5 minutes, and the supernatant was removed using a suction pipette. The centrifuge was then tapped.

After tapping, (the number of plates for cell inoculation)× 10 ml of an RPMI1640 S.P-15% FCS-HAT medium was sprayed thereonto, and the cells were inoculated onto the 96-well plates using an eight-channel micropipette (100 μl each) and a tray designed specifically therefor and using a yellow chip. The cells were cultured at 37° C. for 7 to 14 days in a 5% $CO_2$ incubator. Colony growth was confirmed, and antibody-binding ability was screened by ELISA.

2-4. Selection of Anti-MK Positive Antibody-Producing Hybridomas 10 days after cell fusion, 12 wells that exhibited significantly high absorbance in ELISA were selected from among the supernatants in the 96-well culture plates and used as samples for cloning. The cell count of the hybridomas was measured, and the hybridoma cells were inoculated to a 96-well culture plate in amounts of 5 cells/well (3 rows), 1 cell/well (3 rows), and 0.5 cells/well (2 rows). Moreover, feeder cells were inoculated to the wells in an amount of $1 \times 10^6$ cells/well. On day 5 after cloning, colonies were counted to confirm wells containing one colony. Medium replacement was performed every two to three days. When the colony occupied ⅓ of the well, wells that contained one colony and exhibited a positive reaction were selected using ELISA. Cells obtained from two wells that contained one colony with favorable cell state and were positive in ELISA were designated as hybridomas CSM-1 and CSM-4 and used as established cell lines. Antibodies were prepared by an ascites method using the obtained hybridomas and nude mice and purified on a protein G column.

The antigen solution was prepared to a concentration of 0.1 μg/mL and immobilized on a 96-well assay plate in the same way as above. The antibody titers of the obtained antibodies were measured using this assay plate. As a result, the D450 values of CSM-1 and CSM-4 exhibited 2.5 and 2.6, respectively.

Example 2

Cell Migration Activity Measurement of Mouse Anti-Human MK Monoclonal Antibodies 1. Preparation of MK-Immobilized Chambers The undersurface of Chemotaxicell of 8 in in pore size (manufactured by Kurabo Industries Ltd.) for 24-well plates was turned up, and MK dissolved at a concentration of 20 µg/ml in purified water was added dropwise in an amount of 30 µl/chamber and uniformly spread by means of a tip. The chambers were left standing at room temperature for 1 hour and then washed twice with PBS (phosphate buffered saline).

BSA (manufactured by Sigma-Aldrich Co., A4503) was dissolved at a final concentration of 0.3% in DMEM (Dulbecco's Modified Eagle's medium with 4,500 mg/ml glucose, manufactured by Sigma-Aldrich Co., D5796) and sterilized by filtration through a 0.2-µm filter to obtain a medium (hereinafter, referred to as "0.3% BSA-DMEM"), which was in turn added in an amount of 450 µl/well to a 24-well plate (manufactured by TPP AG, #92424, purchased from BM Medical Equipment). Each mouse anti-human MK antibody obtained in Example 1 was diluted to 100 µg/ml with 0.3% BSA-DMEM and added thereto in an amount of 50 µl (final concentration: 10 µg/ml). To control wells, only 0.3% BSA-DMEM was added in an amount of 50 µl/well. Then, the MK-immobilized Chemotaxicell thus prepared was set in each well.

2. Preparation of Rat Osteoblast-Like Cells UMR106

Rat osteoblast-like cells UMR106 (ATCC No. CRL1661) suspended in 10% FCS-DMEM (Dulbecco's Modified Eagle's medium with 4,500 mg/ml glucose, manufactured by Sigma-Aldrich Co., D5796) were inoculated in an amount of $1 \times 10^6$ cells/10 ml medium/dish to dishes of 10 cm in diameter (manufactured by TPP AG, #93100, purchased from BM Medical Equipment) and cultured at 37° C. for 2 days in a 5% $CO_2$ atmosphere. After culture, the medium was removed, and 3 ml of 0.25% trypsin-EDTA (manufactured by GIBCO, 25200-056) was added thereto. The dishes were left standing at 37° C. for 2 minutes in 5% $CO_2$ atmosphere. The dishes were tapped for cell detachment, and the cells were suspended by the addition of 7 ml of 10% FCS-DMEM (Dulbecco's Modified Eagle's medium with 4,500 mg/ml glucose, manufactured by Sigma-Aldrich Co., 05796) and collected into a centrifuge. An aliquot of the collected cell suspension was collected, and the cell count was measured. The cell count after culture was 4 to $8 \times 10^6$ cells/dish. The remaining cell suspension was centrifuged at 1200 rpm (260×g) for 3 minutes, and the precipitates were collected by suspension in 0.3% BSA-DMEM. The cells were suspended at a concentration of $1 \times 10^6$ cells/ml by the addition of 0.3% BSA-DMEM.

3. Migration Test of Rat Osteoblast-Like Cells UMR106

The cell suspension ($1 \times 10^6$ cells/ml) prepared in the paragraph 2. was added in an amount of 200 µl/chamber ($2 \times 10^5$ cells/chamber) to the inner layer of the Chemotaxicell set in the paragraph 1. and cultured at 37° C. for 4 hours in a 5% $CO_2$ atmosphere. After culture, the cells inside the Chemotaxicell were removed together with the medium. After washing twice with 200 µl of PBS, a paper towel was put on the corners of the undersurface of the chambers for removal of moistures. 100% methanol cooled in a freezer at −20° C. was added in an amount of 500 µl/well to a 24-well plate, and the Chemotaxicell was set therein. The plate was left standing at room temperature for 20 minutes. Then, the inside surface of the Chemotaxicell was washed by swabbing. A 1% aqueous crystal violet solution was added in an amount of 100 µl/well to a 24-well plate, and the Chemotaxicell was set therein such that only the outer surface of the chambers came into contact with the dye. The plate was left standing at room temperature for 30 minutes. Then, a paper towel was put on the corners of the undersurface of the chambers for removal of the dye. Then, the chambers were washed by dipping in a 500-ml beaker filled with water. The chambers were left standing overnight at room temperature for drying. Then, 1% SDS and 1% Triton X-100 were added in an amount of 200 µl/well to a 24-well plate, and the Chemotaxicell was set therein. After shaking at room temperature for 1 hour, a 150 µl aliquot thereof was transferred to a 96-well plate (manufactured by NUNC, #469957), and OD (590 nm; POWERSCAN HT, manufactured by Dainippon Sumitomo Pharma Co., Ltd.) was measured. The ratio (%) of the OD value of the antibody-supplemented sample to that of the antibody-nonsupplemented sample (control) was calculated to evaluate antibody activities.

The results are shown in Table 1. As shown in Table 1, the antibody of the present invention significantly inhibited cell infiltration induced by MK. The present results demonstrated that the antibody of the present invention can be used as therapeutic and preventive drugs for various diseases attributed to cell migration involving MK.

TABLE 1

| | UMR106 cell infiltration (% of control) | |
|---|---|---|
| | CSM-1 | CSM-4 |
| Average value ± standard deviation | 41.0 ± 22.1 | 31.5 ± 1.7 |

Example 3

Analysis of Epitopes on Human MK

1. Preparation of Inserts

PCR of 30 cycles each involving temperature change of 94° C.→55° C.→72° C. was performed using, as templates, plasmids comprising a human MK coding region cloned in pcDNA3.1(−) (manufactured by Invitrogen Corp., V795-20) as well as sense PCR primer:

```
                                      (SEQ ID No: 5)
5'-AAAAAGAAAGATAAGGTGAAGAAGGGCGGCCCG-3', (SEQ ID No: 6)
5'-AAGAAGGGCGGCCCGGGGAGCGAGTGC-3', (SEQ ID No: 7)
5'-TGCGCTGAGTGGGCCTGGGGG-3', (SEQ ID No: 8)
5'-TGCAAGTACAAGTTTGAGAACTGGGGT-3'
and anti-sense PCR primer:
                                      (SEQ ID No: 9)
5'-AGTTCTCGAGTCAATGATGATGATGATGATGGTCCTTTCCCTT
CCCTTT-3', (SEQ ID No: 10)
5'-AGTTCTCGAGTCAATGATGATGATGATGATGGTCGGCTCCAAA
CTCCTT-3', (SEQ ID No: 11)
5'-AGTTCTCGAGTCAATGATGATGATGATGATGATGGGGCACCCT
GCACCGGAT-3', (SEQ ID No: 12)
5'-AGTTCTCGAGTCAATGATGATGATGATGATGGCAGGGCTTGGT
GACGCG-3'
``` comprising a histidine (His×6) tag sequence, a stop codon, and a sequence recognized by a restriction enzyme XhoI (5'-CTCGAG-3') to prepare inserts MK_1-121 (full-length MK), MK_1-61 (N-fragment+loop), MK_7-51, MK_15-61 (N-domain+loop), MK_15-51 (N-domain except for Cys52), MK_62-121 (C-fragment), and MK_62-104 (C-domain) (in this context, the term "MK_a-b" represents DNA encoding a peptide having an amino acid sequence from amino acid residue a to amino acid residue b of MK).

Moreover, by two-step PCR (overlap extension), alanine point mutation was introduced in the N-domain portion of the N-fragment+loop (MK_1-61) to prepare inserts MK_1-61 (W18A), MK_1-61 (W20A), MK_1-61 (P22A), MK_1-61 (T24A+P25A), MK_1-61 (S26A), MK_1-61 (S27A), MK_1-61 (K28A), MK_1-61 (V32A), MK_1-61 (F34A), MK_1-61 (R35A), MK_1-61 (E36A), MK_1-61 (T38A), MK_1-61 (Q42A), MK_1-61 (T43A), MK_1-61 (Q44A), MK_1-61 (R45A), MK_1-61 (I46A), MK_1-61 (R47A), MK_1-61 (R49A) and alanine point mutation was introduced in the C-domain portion of the C-fragment (MK_62-121) to prepare inserts MK_62-121 (K63A), MK_62-121 (Y64A), MK_62-121 (K65A), MK_62-121 (F66A), MK_62-121 (E67A), MK_62-121 (N68A), MK_62-121 (W69A), MK_62-121 (D73A), MK_62-121 (R81A), MK_62-121 (T84A), MK_62-121 (K86A), MK_62-121 (K87A), MK_62-121 (R89A), MK_62-121 (Y90A), MK_62-121 (Q93A), MK_62-121 (Q95A), MK_62-121 (E96A), MK_62-121 (R99A), and MK_62-121 (K102A) (in this context, the term "MK_a-b(XcY)" (a, b, and c represent a number, and X and Y represent an uppercase alphabetic character) represents DNA encoding a peptide which has an amino acid sequence from amino acid residue a to amino acid residue b of MK and has mutation from X to Y at amino acid residue c of MK; X and Y are indicated in a single character code of the amino acid).

These inserts were blunt-ended at both the termini using DNA Blunting Kit (manufactured by TAKARABIO INC., 6025) and then treated with a restriction enzyme XhoI (manufactured by TAKARABIO INC., 1094A; the same holds true for description below) to form 3'-protruding ends.

2. Preparation of Plasmid Vectors

Next, pGEX-6P-2 (manufactured by GE Healthcare, 27-4598-01) plasmid vectors were treated with restriction enzymes SmaI (manufactured by Toyobo Co., Ltd., SMA-111T) and XhoI. To the vectors thus treated (SmaI-cleaved site was blunt-ended), each insert prepared in the paragraph 1. was inserted using DNA Ligation Kit Ver. 1 (manufactured by TAKARABIO INC., 6025) to prepare plasmid vectors having a start codon and a GST coding region before the MK sequence.

Competent high E. coli JM109 (manufactured by Toyobo Co., Ltd., DNA-900) was transformed with the prepared plasmid vectors by heat treatment at 42° C. for 30 seconds in a water bath according to a heat shock method. These cells were inoculated onto 100 μg/ml ampicillin-LB (Luria-Bertani) media and left standing overnight at 37° C. to obtain plural single colonies. Each single colony was cultured overnight at 37° C. in 7 ml of a 100 μg/ml ampicillin-LB medium, and plasmids were purified by a Mini Prep method (see J. Sambrook and D. W. Russell: Molecular Cloning: a laboratory manual, 3rd ed. (2001) Vol. 1, p 1.32-1.34). The DNA sequences of these plasmids were analyzed (manufactured by Applied Biosystems, Inc., 3730×1 DNA Analyzer) using a pGEX5' sequencing primer (manufactured by GE Healthcare, 27-1410-01) for the vectors to select single colonies having the plasmid of interest.

The single colony was added to 2 ml of a 100 μg/ml ampicillin-LB medium and cultured overnight at 37° C. 20 μl of the culture solution was transferred to 2 ml of a 100 μg/ml ampicillin-LB medium and cultured at 37° C. for 2 hours. Then, IPTG was added thereto at a final concentration of 0.2 mM for induction at 37° C. for 2 hours to obtain the protein of interest. A 1 ml aliquot was collected from this culture solution and centrifuged at 1,900 g for 3 minutes. The supernatant was discarded, and the precipitates were dispersed in 200 μl of a sample buffer (4% SDS, 10% mercaptoethanol, 10% glycerol, and 0.1 M Tris-HCl, pH 7.2) and sonicated for 10 seconds three times.

3. Epitope Measurement of Mouse Anti-Human MK Monoclonal Antibodies 3.5 μl each of the full-length MK, the partial MK (MK_1-61, MK_15-61, MK_7-51, MK_15-51, MK_62-121, and MK_62-104), and the alanine mutants of MK_1-61 and MK_62-121 was loaded on two 12% polyacrylamide gels with the same patterns for electrophoresis. The first gel was stained with CBB (Coomassie Brilliant Blue) to confirm whether expression levels were almost equal among the proteins. The second gel was transferred to a PVDF membrane by a semi-dry approach (6 V, 2.5 h). This PVDF membrane was blocked at room temperature for 2 hours with 5% skim milk-0.05% Tween 20-PBS. Then, 0.05% Tween 20-PBS containing 2 μg/ml of the mouse monoclonal anti-MK antibody obtained in Example 1 was added thereto, and the membrane was left standing overnight at 4° C. The membrane was washed for 10 minutes three times with 0.05% Tween 20-PBS. Then, 1/10,000 anti-mouse IgG (peroxidase-conjugated; manufactured by PIERCE, 31452)-0.05% Tween 20-PBS was added thereto, and the membrane was left standing at room temperature for 1 hour. The membrane was further washed for 10 minutes three times with 0.05% Tween 20-PBS. Then, color development was performed using TMB Membrane Peroxidase Substrate System (manufactured by Kirkegaard & Perry Laboratories: KPL, 50-77-00).

Color intensity was compared among the full length MK, the partial MK (MK_1-61, MK_15-61, MK_7-51, MK_15-51, MK_62-121, and MK_62-104), and the alanine mutants of MK_1-61 and MK_62-121 to identify epitope-containing sites. When the N- or C-domain contained an epitope, color intensity was compared between the alanine mutants within the domain of MK_1-61 or MK_62-121 and their respective wild types (without mutation) to examine the extent to which the amino acid residue with alanine point mutation participated in the epitope.

Figure 3:
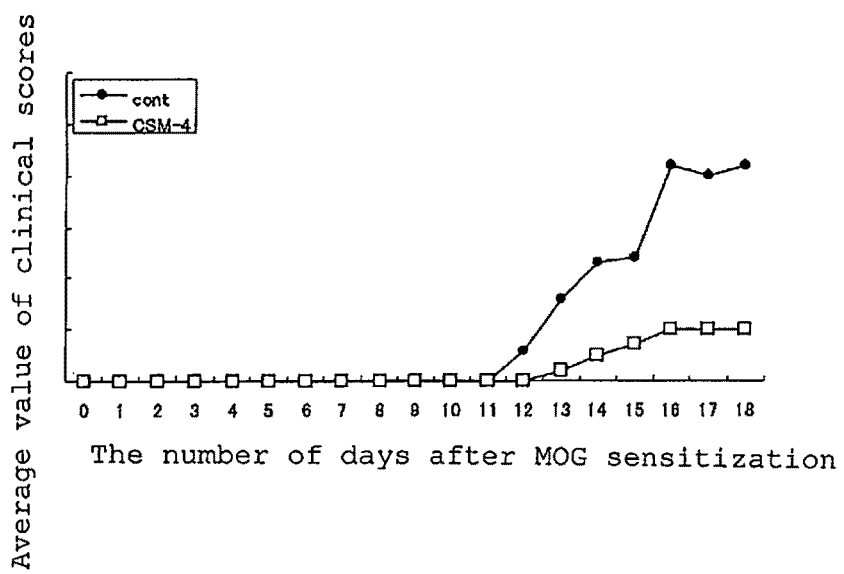
FIG. 3 shows scores of EAE model mice to which CSM-4 has been administered. The ordinate represents an average value of clinical scores of each group. The abscissa represents the number of days after MOG sensitization. Moreover, in the diagram, the black circle represents a control, and the open triangle represents CSM-4-administered mice.

The results are shown in FIG. 3. The present results demonstrated that the CSM-1 antibody recognizes tyrosine 64, lysine 65, lutamic acid 67, threonine 84, lysine 86, phenylalanine 66, tryptophan 69, aspartic acid 73, and glutamic acid 96 (particularly, tyrosine 64, lysine 65, μlutamic acid 67, threonine 84, and lysine 86) of MK, because of large reduction in the antigenicity of tyrosine 64, lysine 65, μlutamic acid 67, threonine 84, and lysine 86 of MK and reduction in the antigenicity of phenylalanine 66, tryptophan 69, aspartic acid 73, and glutamic acid 96 of MK.

The results also demonstrated that the CSM-4 antibody recognizes tyrosine 64, lysine 87, tyrosine 90, phenylalanine 66, and glutamic acid 96 (particularly, tyrosine 64, lysine 87, and tyrosine 90) of MK, because of large reduction in the antigenicity of tyrosine 64, lysine 87, and tyrosine 90 of MK and reduction in the antigenicity of phenylalanine 66 and glutamic acid 96 of MK.

Example 4

Analysis of CDR Sequences of CSM-1 and CSM-4

The CDR sequences of the mouse anti-human MK monoclonal antibodies CSM-1 and CSM-4 obtained in Example 1 were analyzed by a method well known to those skilled in the art (see Johansson et al., J. Exp. Med., 180, pp. 1873-1888 (1994) and Orlandi et al., Proc. Natl. Acad. Sci. USA, 86, pp. 3833-3837 (1989)). As a result, CSM-1 had heavy chain CDR sequences of CDR1: DYFLH (SEQ ID NO: 13), CDR2: RIDPEDSETKYAPKFQG (SEQ ID NO: 14), and CDR3: NYGGGGFAY (SEQ ID NO: 15), and light chain CDR sequences of CDR1: KASQDVSTAVA (SEQ ID NO: 16), CDR2: SASYRYT (SEQ ID NO: 17), and CDR3: QQHYSSPFT (SEQ ID NO: 18). Moreover, CSM-4 had heavy chain CDR sequences of CDR1: SYWMN (SEQ ID NO: 19), CDR2: MIHPSDSETILNQKFKD (SEQ ID NO: 20), and CDR3: WSAKRGDF (SEQ ID NO: 21), and light chain CDR sequences of CDR1: RASESISNNLH (SEQ ID NO: 22), CDR2: YASQSIS (SEQ ID NO: 23), and CDR3: QQSNSWPLT (SEQ ID NO: 24).

Example 5

EAE Model Animal Test of Mouse Anti-Human MK Monoclonal Antibodies

1. Preparation of Myelin Oligodendrocyte Glycoprotein Peptide (MOG) Emulsion 10 mg of a myelin oligodendrocyte glycoprotein peptide 35-55 (MOG, Toray Research Center, Inc., sequence: MEVGWYRSPFSRVVHLYRNGK; SEQ ID NO:25) was dissolved in 5 mL of pure water to prepare a 2 mg/mL MOG peptide solution. *Mycobacterium tuberculosis* (MTB; Difco) was added to a complete Freund's adjuvant (CFA, Sigma-Aldrich Co.) containing 1 mg/mL heat-killed MTB H37Ra to prepare an MTB-CFA solution containing 3 mg/mL MTB. To the MOG peptide solution, an equal amount of the MTB-CFA solution was added and mixed until emulsification. One drop of the mixture was added onto water contained in a beaker to confirm the emulsification based on the absence of dispersion.

2. MOG Sensitization

Mice used were 7-week-old female C57BL/6JJcl mice (Fuji Breeding Center, CLEA Japan, Inc.). After receipt, the mice were bred for 8 days to confirm the absence of abnormalities in appearance and behavior. The mice after becoming 8 week old were anesthetized by the intraperitoneal administration of Somnopentyl (pentobarbital sodium, Kyoritsu Seiyaku Corp.) diluted 5-fold with a saline at a dose of 100 μL/mouse. The dorsal to lumbar regions of the mice were sheared, and the MOG emulsion prepared in the paragraph 1. was hypodermically injected to 4 spots at a dose of 50 μL/spot. The mice after recovering from anesthesia received intraperitoneal administration of 100 μL of 0.2 mg/mL pertussis toxin in a 50% glycerol solution (PTX, Sigma-Aldrich Co.) diluted 100-fold (final concentration: 2 μg/mL) with a saline. Two days later (the MOG sensitization day: day 0), they received intraperitoneal administration of PTX in the same amount.

3. Antibody Administration

After MOG sensitization and PTX administration, the body weights of the mice were measured, and the mice were classified into a control group and each antibody-administered group such that each group contained 4 mice with the equally distributed degree of body weights. Each antibody (CSM-1 or CSM-4) was diluted to 1 mg/mL with a saline (Otsuka Pharmaceutical Co., Ltd.) and intraperitoneally administered at a dose of 200 μL per 20 g of mouse body weight (10 mg/kg of body weight). A total of 5 administrations were performed on days 0, 4, 7, 11, and 14 (the MOG sensitization day: day 0). A saline free from the antibodies was administered to the control group at a dose of 200 μL per 20 g of mouse body weight.

4. Observation of Pathological Conditions

After sensitization, the pathological conditions of the mice were observed every day. The pathological conditions were assessed according to the following clinical scores:

Clinical Score
0: no symptom
0.5: slightly limp tail
1: limp tail
2: slight difficulty in righting, slight waddling with their heads tilting
3: walking without lifting their hips off the ground, difficulty in righting
4: walking without lifting their chests off the ground, fore limb weakness, sometimes walking with turning their heads and trunks
5: complete hind limb paralysis
6: moribund or death.

5. Results

The results of administration of the CSM-1 antibody are shown in FIG. 4, and the results of administration of the CSM-4 antibody are shown in FIG. 5. As shown in the diagrams, both the CSM-1 and CSM-4 administrations inhibited the disease onset in the EAE model mice. Since the EAE model mice are used as models of multiple sclerosis, the present experimental results demonstrated that CSM-1 and CSM-4 have therapeutic and preventive effects on multiple sclerosis.

Example 6

Examination of Binding Sites of Mouse Anti-Human MK Monoclonal Antibodies

The three-dimensional structure of MK was obtained from Protein Data Bank, and electrostatic potentials of MK were calculated using Pymol (ver. 0.99). The relationship of the calculated electrostatic potentials with the epitopes (obtained in Example 3) recognized by CSM-1 and CSM-4 was examined. As a result, it was demonstrated that both the antibodies recognize three amino acids of high electrostatic potential sites formed by amino acid residues 62 to 64, amino acid residue 66, amino acid residues 68 to 70, amino acid residue 72, amino acid residue 79, amino acid residue 81, amino acid residues 85 to 89, amino acid residue 102, and amino acid residue 103. Moreover, it was demonstrated that the antibodies recognize, of these high electrostatic potential sites, particularly, one amino acid of positively charged amino acids lysine 63, lysine 79, arginine 81, lysine 86, lysine 87, arginine 89, and lysine 102. These results demonstrated that the effects of CSM-1 and CSM-4 are exerted by their binding to the high electrostatic potential site of MK.

INDUSTRIAL APPLICABILITY

An antibody of the present invention or a fragment thereof inhibits MK functions and is therefore useful as a therapeutic or preventive agent for MK-related disease. Moreover, the antibody of the present invention is useful as a diagnostic agent for MK-related disease.

The invention claimed is:

1. An isolated anti-midkine antibody or an antigen-binding fragment thereof, wherein heavy chain CDR1 has the amino acid sequence represented by SEQ ID NO: 13, heavy chain CDR2 has the amino acid sequence represented by SEQ ID NO: 14, heavy chain CDR3 has the amino acid sequence represented by SEQ ID NO: 15, light chain CDR1 has the amino acid sequence represented by SEQ ID NO: 16, light chain CDR2 has the amino acid sequence represented by SEQ ID NO: 17, and light chain CDR3 has the amino acid sequence represented by SEQ ID NO: 18.

2. A pharmaceutical composition comprising the isolated antibody or antigen-binding fragment thereof according to claim 1.

3. A pharmaceutical composition for prevention or treatment of disease attributed to cell migration, autoimmune disease, cancer, inflammatory disease, or multiple sclerosis, comprising the isolated antibody or antigen-binding fragment thereof according to claim 1.

4. An in vitro cell line which produces the antibody according to claim 1 or an antigen-binding fragment thereof.

5. A method for screening a test compound that binds to midkine for competitive binding with the antibody according to claim 1 or the antigen-binding fragment thereof, comprising the steps of:
(i) contacting the antibody according to claim 1 or the antigen-binding fragment thereof separately with midkine and with midkine in presence of the test compound;
(ii) measuring binding between the antibody according to claim 1 or the antigen-binding fragment thereof and the midkine in the absence and the presence of the test compound;
(iii) determining whether there is a reduction in binding between the antibody according to claim 1 or the antigen-binding fragment thereof and the midkine in the presence of the test compound when compared to the absence of the test compound; and
(iv) selecting the test compound if the presence thereof results in a reduction in binding between the antibody according to claim 1 or the antigen-binding fragment thereof and the midkine thereby identifying the test compound as a binder that competes with the antibody for binding to midkine.

6. An isolated anti-midkine antibody, wherein heavy chain CDR1 has the amino acid sequence represented by SEQ ID NO: 13, heavy chain CDR2 has the amino acid sequence represented by SEQ ID NO: 14, heavy chain CDR3 has the amino acid sequence represented by SEQ ID NO: 15, light chain CDR1 has the amino acid sequence represented by SEQ ID NO: 16, light chain CDR2 has the amino acid sequence represented by SEQ ID NO: 17, and light chain CDR3 has the amino acid sequence represented by SEQ ID NO: 18.

7. An isolated anti-midkine antibody or an antigen-binding fragment thereof, wherein heavy chain CDR1 has the amino acid sequence represented by SEQ ID NO: 19, heavy chain CDR2 has the amino acid sequence represented by SEQ ID NO: 20, heavy chain CDR3 has the amino acid sequence represented by SEQ ID NO: 21, light chain CDR1 has the amino acid sequence represented by SEQ ID NO: 22, light chain CDR2 has the amino acid sequence represented by SEQ ID NO: 23, and light chain CDR3 has the amino acid sequence represented by SEQ ID NO: 24.

8. A pharmaceutical composition comprising the isolated antibody or antigen-binding fragment thereof according to claim 7.

9. A pharmaceutical composition for prevention or treatment of disease attributed to cell migration, autoimmune disease, cancer, inflammatory disease, or multiple sclerosis, comprising the isolated antibody or antigen-binding fragment thereof according to claim 7.

10. An in vitro cell line which produces the antibody according to claim 7 or an antigen-binding fragment thereof.

11. A method for screening a test compound that binds to midkine for competitive binding with the antibody according to claim 7 or the antigen-binding fragment thereof, comprising the steps of:
(i) contacting the antibody according to claim 7 or the antigen-binding fragment thereof separately with midkine and with midkine in presence of the test compound;
(ii) measuring binding between the antibody according to claim 7 or the antigen-binding fragment thereof and the midkine in the absence and the presence of the test compound;
(iii) determining whether there is a reduction in binding between the antibody according to claim 7 or the antigen-binding fragment thereof and the midkine in the presence of the test compound when compared to the absence of the test compound; and
(iv) selecting the test compound if the presence thereof results in a reduction in binding between the antibody according to claim 7 or the antigen-binding fragment thereof and the midkine thereby identifying the test compound as a binder that competes with the antibody for binding to midkine.

12. An isolated anti-midkine antibody, wherein heavy chain CDR1 has the amino acid sequence represented by SEQ ID NO: 19, heavy chain CDR2 has the amino acid sequence represented by SEQ ID NO: 20, heavy chain CDR3 has the amino acid sequence represented by SEQ ID NO: 21, light chain CDR1 has the amino acid sequence represented by SEQ ID NO: 22, light chain CDR2 has the amino acid sequence represented by SEQ ID NO: 23, and light chain CDR3 has the amino acid sequence represented by SEQ ID NO: 24.

* * * * *

SEQUENCE LISTING

<160> NUMBER OF SEQ ID NOS: 25

<210> SEQ ID NO 1
<211> LENGTH: 866
<212> TYPE: DNA
<213> ORGANISM: Homo sapiens
<220> FEATURE:
<221> NAME/KEY: CDS
<222> LOCATION: (92)..(520)
<220> FEATURE:
<221> NAME/KEY: mat_peptide
<222> LOCATION: (158)..(520)

<400> SEQUENCE: 1

```
agaccggttc tggagacaaa aggggccgcg gcggccggag cgggacgggc ccggcgcggg      60
agggagcgaa gcagcgcggg cagcgagcga g atg cag cac cga ggc ttc ctc       112
                                   Met Gln His Arg Gly Phe Leu
                                                       -20 ctc ctc acc ctc ctc gcc ctg ctg gcg ctc acc tcc gcg gtc gcc aaa      160
Leu Leu Thr Leu Leu Ala Leu Leu Ala Leu Thr Ser Ala Val Ala Lys
-15              -10                 -5                  -1  1 aag aaa gat aag gtg aag aag ggc ggc ccg ggg agc gag tgc gct gag      208
Lys Lys Asp Lys Val Lys Lys Gly Gly Pro Gly Ser Glu Cys Ala Glu
          5                   10                  15 tgg gcc tgg ggg ccc tgc acc ccc agc agc aag gat tgc ggc gtg ggt      256
Trp Ala Trp Gly Pro Cys Thr Pro Ser Ser Lys Asp Cys Gly Val Gly
         20                  25                  30 ttc cgc gag ggc acc tgc ggg gcc cag acc cag cgc atc cgg tgc agg      304
Phe Arg Glu Gly Thr Cys Gly Ala Gln Thr Gln Arg Ile Arg Cys Arg
     35                  40                  45 gtg ccc tgc aac tgg aag aag gag ttt gga gcc gac tgc aag tac aag      352
Val Pro Cys Asn Trp Lys Lys Glu Phe Gly Ala Asp Cys Lys Tyr Lys
50                   55                  60                  65 ttt gag aac tgg ggt gcg tgt gat ggg ggc aca ggc acc aaa gtc cgc      400
Phe Glu Asn Trp Gly Ala Cys Asp Gly Gly Thr Gly Thr Lys Val Arg
                 70                  75                  80 caa ggc acc ctg aag aag gcg cgc tac aat gct cag tgc cag gag acc      448
Gln Gly Thr Leu Lys Lys Ala Arg Tyr Asn Ala Gln Cys Gln Glu Thr
             85                  90                  95 atc cgc gtc acc aag ccc tgc acc ccc aag acc aaa gca aag gcc aaa      496
Ile Arg Val Thr Lys Pro Cys Thr Pro Lys Thr Lys Ala Lys Ala Lys
         100                 105                 110 gcc aag aaa ggg aag gga aag gac tagacgccaa gcctggatgc caaggagccc      550
Ala Lys Lys Gly Lys Gly Lys Asp
     115                 120 ctggtgtcac atggggcctg gcccacgccc tccctctccc aggcccgaga tgtgacccac      610
cagtgccttc tgtctgctcg ttagctttaa tcaatcatgc cctgccttgt ccctctcact      670
ccccagcccc acccctaagt gcccaaagtg gggagggaca agggattctg ggaagcttga      730
gcctccccca aagcaatgtg agtcccagag cccgcttttg ttcttcccca caattccatt      790
actaagaaac acatcaaata aactgacttt ttcccccccaa taaaagctct tcttttttaa      850
tataaaaaaa aaaaaa                                                     866
```

<210> SEQ ID NO 2
<211> LENGTH: 143
<212> TYPE: PRT
<213> ORGANISM: Homo sapiens

<400> SEQUENCE: 2

| Met | Gln | His | Arg | Gly | Phe | Leu | Leu | Thr | Leu | Leu | Ala | Leu | Leu | Ala |
|---|---|---|---|---|---|---|---|---|---|---|---|---|---|---|
| | | | -20 | | | | -15 | | | | -10 | | | |

| Leu | Thr | Ser | Ala | Val | Ala | Lys | Lys | Asp | Lys | Val | Lys | Lys | Gly | Gly |
|---|---|---|---|---|---|---|---|---|---|---|---|---|---|---|
| | -5 | | | | -1 | 1 | | | 5 | | | | | 10 |

| Pro | Gly | Ser | Glu | Cys | Ala | Glu | Trp | Ala | Trp | Gly | Pro | Cys | Thr | Pro | Ser |
|---|---|---|---|---|---|---|---|---|---|---|---|---|---|---|---|
| | | | | 15 | | | | | 20 | | | | | 25 | |

| Ser | Lys | Asp | Cys | Gly | Val | Gly | Phe | Arg | Glu | Gly | Thr | Cys | Gly | Ala | Gln |
|---|---|---|---|---|---|---|---|---|---|---|---|---|---|---|---|
| | | | 30 | | | | | 35 | | | | | 40 | | |

Thr Gln Arg Ile Arg Cys Arg Val Pro Cys Asn Trp Lys Lys Glu Phe
              45                  50                  55

Gly Ala Asp Cys Lys Tyr Lys Phe Glu Asn Trp Gly Ala Cys Asp Gly
        60                  65                  70

Gly Thr Gly Thr Lys Val Arg Gln Gly Thr Leu Lys Lys Ala Arg Tyr
75              80              85              90

Asn Ala Gln Cys Gln Glu Thr Ile Arg Val Thr Lys Pro Cys Thr Pro
            95                  100                 105

Lys Thr Lys Ala Lys Ala Lys Ala Lys Lys Gly Lys Gly Lys Asp
            110                 115                 120

<210> SEQ ID NO 3
<211> LENGTH: 30
<212> TYPE: DNA
<213> ORGANISM: Artificial Sequence
<220> FEATURE:
<223> OTHER INFORMATION: Synthetic MK sense primer

<400> SEQUENCE: 3
gcggaattca tgcagcaccg aggcttcctc                                      30

<210> SEQ ID NO 4
<211> LENGTH: 30
<212> TYPE: DNA
<213> ORGANISM: Artificial Sequence
<220> FEATURE:
<223> OTHER INFORMATION: Synthetic MK antisense primer

<400> SEQUENCE: 4
gcggaattcc tagtcctttc ccttcccttt                                      30

<210> SEQ ID NO 5
<211> LENGTH: 33
<212> TYPE: DNA
<213> ORGANISM: Artificial Sequence
<220> FEATURE:
<223> OTHER INFORMATION: Synthetic sense primer

<400> SEQUENCE: 5
aaaaagaaag ataaggtgaa gaagggcggc ccg                                  33

<210> SEQ ID NO 6
<211> LENGTH: 27
<212> TYPE: DNA
<213> ORGANISM: Artificial Sequence
<220> FEATURE:
<223> OTHER INFORMATION: Synthetic sense primer

<400> SEQUENCE: 6
aagaagggcg gcccggggag cgagtgc                                         27

<210> SEQ ID NO 7
<211> LENGTH: 21
<212> TYPE: DNA
<213> ORGANISM: Artificial Sequence
<220> FEATURE:
<223> OTHER INFORMATION: Synthetic sense primer

<400> SEQUENCE: 7
tgcgctgagt gggcctgggg g                                    21

<210> SEQ ID NO 8
<211> LENGTH: 27
<212> TYPE: DNA
<213> ORGANISM: Artificial Sequence
<220> FEATURE:
<223> OTHER INFORMATION: Synthetic sense primer

<400> SEQUENCE: 8
tgcaagtaca agtttgagaa ctggggt                              27

<210> SEQ ID NO 9
<211> LENGTH: 49
<212> TYPE: DNA
<213> ORGANISM: Artificial Sequence
<220> FEATURE:
<223> OTHER INFORMATION: Synthetic antisense primer with His Tag

<400> SEQUENCE: 9
agttctcgag tcaatgatga tgatgatgat ggtcctttcc cttcccttt      49

<210> SEQ ID NO 10
<211> LENGTH: 49
<212> TYPE: DNA
<213> ORGANISM: Artificial Sequence
<220> FEATURE:
<223> OTHER INFORMATION: Synthetic antisense primer with His Tag

<400> SEQUENCE: 10
agttctcgag tcaatgatga tgatgatgat ggtcggctcc aaactcctt      49

<210> SEQ ID NO 11
<211> LENGTH: 49
<212> TYPE: DNA
<213> ORGANISM: Artificial Sequence
<220> FEATURE:
<223> OTHER INFORMATION: Synthetic antisense primer with His Tag

<400> SEQUENCE: 11
agttctcgag tcaatgatga tgatgatgat ggggcaccct gcaccggat      49

<210> SEQ ID NO 12
<211> LENGTH: 49
<212> TYPE: DNA
<213> ORGANISM: Artificial Sequence
<220> FEATURE:
<223> OTHER INFORMATION: Synthetic antisense primer with His Tag

<400> SEQUENCE: 12
agttctcgag tcaatgatga tgatgatgat ggcagggctt ggtgacgcg      49

<210> SEQ ID NO 13
<211> LENGTH: 5
<212> TYPE: PRT
<213> ORGANISM: Mus musculus

<400> SEQUENCE: 13

Asp Tyr Phe Leu His
1               5

<210> SEQ ID NO 14
<211> LENGTH: 17
<212> TYPE: PRT
<213> ORGANISM: Mus musculus

<400> SEQUENCE: 14

Arg Ile Asp Pro Glu Asp Ser Glu Thr Lys Tyr Ala Pro Lys Phe Gln
1               5                   10                  15

Gly

<210> SEQ ID NO 15
<211> LENGTH: 9
<212> TYPE: PRT
<213> ORGANISM: Mus musculus

<400> SEQUENCE: 15

Asn Tyr Gly Gly Gly Gly Phe Ala Tyr
1               5

<210> SEQ ID NO 16
<211> LENGTH: 11
<212> TYPE: PRT
<213> ORGANISM: Mus musculus

<400> SEQUENCE: 16

Lys Ala Ser Gln Asp Val Ser Thr Ala Val Ala
1               5                   10

<210> SEQ ID NO 17
<211> LENGTH: 7
<212> TYPE: PRT
<213> ORGANISM: Mus musculus

<400> SEQUENCE: 17

Ser Ala Ser Tyr Arg Tyr Thr
1               5

<210> SEQ ID NO 18
<211> LENGTH: 9
<212> TYPE: PRT
<213> ORGANISM: Mus musculus

<400> SEQUENCE: 18

Gln Gln His Tyr Ser Ser Pro Phe Thr
1               5

<210> SEQ ID NO 19
<211> LENGTH: 5
<212> TYPE: PRT
<213> ORGANISM: Mus musculus

<400> SEQUENCE: 19

Ser Tyr Trp Met Asn
1               5

<210> SEQ ID NO 20
<211> LENGTH: 17
<212> TYPE: PRT
<213> ORGANISM: Mus musculus

```
<400> SEQUENCE: 20

Met Ile His Pro Ser Asp Ser Glu Thr Ile Leu Asn Gln Lys Phe Lys
1               5                   10                  15

Asp

<210> SEQ ID NO 21
<211> LENGTH: 8
<212> TYPE: PRT
<213> ORGANISM: Mus musculus

<400> SEQUENCE: 21

Trp Ser Ala Lys Arg Gly Asp Phe
1               5

<210> SEQ ID NO 22
<211> LENGTH: 11
<212> TYPE: PRT
<213> ORGANISM: Mus musculus

<400> SEQUENCE: 22

Arg Ala Ser Glu Ser Ile Ser Asn Asn Leu His
1               5                   10

<210> SEQ ID NO 23
<211> LENGTH: 7
<212> TYPE: PRT
<213> ORGANISM: Mus musculus

<400> SEQUENCE: 23

Tyr Ala Ser Gln Ser Ile Ser
1               5

<210> SEQ ID NO 24
<211> LENGTH: 9
<212> TYPE: PRT
<213> ORGANISM: Mus musculus

<400> SEQUENCE: 24

Gln Gln Ser Asn Ser Trp Pro Leu Thr
1               5

<210> SEQ ID NO 25
<211> LENGTH: 21
<212> TYPE: PRT
<213> ORGANISM: Mus musculus

<400> SEQUENCE: 25

Met Glu Val Gly Trp Tyr Arg Ser Pro Phe Ser Arg Val Val His Leu
1               5                   10                  15

Tyr Arg Asn Gly Lys
            20
```